(12) United States Patent
Humphreys et al.

(10) Patent No.: US 7,771,479 B2
(45) Date of Patent: Aug. 10, 2010

(54) DUAL ARTICULATING SPINAL DEVICE AND METHOD

(75) Inventors: Steven C. Humphreys, Chattanooga, TN (US); Scott D. Hodges, Ooltewah, TN (US); Marc M. Peterman, Memphis, TN (US); Danny H. Braddock, Jr., Bartlett, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1460 days.

(21) Appl. No.: 11/031,603

(22) Filed: Jan. 7, 2005

(65) Prior Publication Data

US 2005/0154461 A1 Jul. 14, 2005

Related U.S. Application Data

(60) Provisional application No. 60/534,960, filed on Jan. 9, 2004.

(51) Int. Cl.
*A61F 2/44* (2006.01)
(52) U.S. Cl. .................................. 623/17.15
(58) Field of Classification Search ... 623/17.11–17.16; 606/60, 246–249
See application file for complete search history.

(56) References Cited

U.S. PATENT DOCUMENTS

| | | | |
|---|---|---|---|
| 4,349,921 A | 9/1982 | Kuntz | |
| 4,697,582 A | 10/1987 | Williams | |
| 4,759,769 A * | 7/1988 | Hedman et al. .......... 623/17.13 |
| 5,092,866 A | 3/1992 | Breard et al. | |
| 5,258,031 A | 11/1993 | Salib et al. | |
| 5,282,863 A | 2/1994 | Burton | |
| 5,387,213 A | 2/1995 | Breard et al. | |
| 5,401,269 A | 3/1995 | Buttner-Janz et al. | |
| 5,415,661 A | 5/1995 | Holmes | |
| 5,507,816 A | 4/1996 | Bullivant | |
| 5,556,431 A | 9/1996 | Buttner-Janz | |
| 5,562,660 A | 10/1996 | Grob | |
| 5,562,737 A | 10/1996 | Graf | |

(Continued)

FOREIGN PATENT DOCUMENTS

DE 101 35771 A1 2/2003

(Continued)

OTHER PUBLICATIONS

Patent Cooperation Treaty—European Patent Office, "Notification of Transmittal of the International Search Report and the Written Opinion of the Internatinal Searching Authority, or the Declaration," International Application No. PCT/US2005/000648, Jun. 6, 2005, 6 pages.

(Continued)

*Primary Examiner*—Thomas C Barrett
*Assistant Examiner*—Michael J Araj

(57) ABSTRACT

An artificial spinal joint creates at least a portion of a coupling between a superior vertebra and an inferior vertebra. The artificial spinal joint comprises an anterior joint replacement component extending into an intervertebral disc space between the superior and inferior vertebrae. The artificial spinal joint further comprises a bridge component coupled to the anterior joint replacement and extending posteriorly from the anterior joint replacement beyond the intervertebral disc space and a posterior joint replacement component coupled to the bridge, wherein the posterior joint replacement component includes a posterior protrusion engaged with a posterior socket.

29 Claims, 10 Drawing Sheets

U.S. PATENT DOCUMENTS

| | | | |
|---|---|---|---|
| 5,562,738 A | 10/1996 | Boyd et al. | |
| 5,672,175 A | 9/1997 | Martin | |
| 5,674,296 A * | 10/1997 | Bryan et al. | 623/17.16 |
| 5,676,701 A | 10/1997 | Yuan et al. | |
| 5,702,450 A | 12/1997 | Bisserie | |
| 5,895,428 A | 4/1999 | Berry | |
| 5,899,941 A | 5/1999 | Nishijima et al. | |
| RE36,221 E | 6/1999 | Breard et al. | |
| 5,961,516 A | 10/1999 | Graf | |
| 6,039,763 A | 3/2000 | Shelokov | |
| RE36,758 E | 6/2000 | Fitz | |
| 6,113,637 A | 9/2000 | Gill et al. | |
| 6,132,464 A | 10/2000 | Martin | |
| 6,146,421 A | 11/2000 | Gordon et al. | |
| 6,156,067 A | 12/2000 | Bryan et al. | |
| 6,179,874 B1 | 1/2001 | Cauthen | |
| 6,179,875 B1 | 1/2001 | Strempel | |
| 6,228,118 B1 | 5/2001 | Gordon | |
| 6,368,350 B1 | 4/2002 | Erickson et al. | |
| 6,402,750 B1 | 6/2002 | Atkinson et al. | |
| 6,419,703 B1 | 7/2002 | Fallin et al. | |
| 6,517,580 B1 | 2/2003 | Ramadan et al. | |
| 6,527,804 B1 | 3/2003 | Gauchet et al. | |
| 6,540,747 B1 | 4/2003 | Marino | |
| 6,540,785 B1 | 4/2003 | Gill et al. | |
| 6,565,571 B1 | 5/2003 | Jackowski et al. | |
| 6,565,605 B2 | 5/2003 | Goble et al. | |
| 6,572,653 B1 | 6/2003 | Simonson | |
| 6,579,319 B2 | 6/2003 | Goble et al. | |
| 6,582,466 B1 | 6/2003 | Gauchet | |
| 6,582,468 B1 | 6/2003 | Gauchet | |
| 6,610,091 B1 | 8/2003 | Reiley | |
| 6,610,093 B1 | 8/2003 | Pisharodi | |
| 6,669,729 B2 | 12/2003 | Chin | |
| 6,679,915 B1 | 1/2004 | Cauthen | |
| 6,811,567 B2 | 11/2004 | Reiley | |
| 6,908,484 B2 * | 6/2005 | Zubok et al. | 623/17.15 |
| 6,949,123 B2 | 9/2005 | Reiley | |
| 6,994,727 B2 | 2/2006 | Khandkar et al. | |
| 7,052,515 B2 | 5/2006 | Simonson | |
| 7,083,649 B2 | 8/2006 | Zucherman et al. | |
| 7,090,698 B2 | 8/2006 | Goble et al. | |
| 2002/0095154 A1 | 7/2002 | Atkinson et al. | |
| 2002/0123806 A1 | 9/2002 | Reiley | |
| 2002/0133155 A1 | 9/2002 | Ferree | |
| 2002/0151895 A1 | 10/2002 | Soboleski et al. | |
| 2003/0004572 A1 | 1/2003 | Goble et al. | |
| 2003/0009226 A1 | 1/2003 | Graf | |
| 2003/0028250 A1 | 2/2003 | Reiley et al. | |
| 2003/0040797 A1 | 2/2003 | Fallin et al. | |
| 2003/0055427 A1 | 3/2003 | Graf | |
| 2003/0139812 A1 | 7/2003 | Garcia et al. | |
| 2003/0139813 A1 | 7/2003 | Messerli et al. | |
| 2003/0191532 A1 | 10/2003 | Goble et al. | |
| 2003/0199981 A1 | 10/2003 | Ferree | |
| 2003/0199982 A1 | 10/2003 | Bryan | |
| 2003/0204259 A1 | 10/2003 | Goble et al. | |
| 2003/0204260 A1 | 10/2003 | Ferree | |
| 2003/0204271 A1 | 10/2003 | Ferree | |
| 2003/0233146 A1 | 12/2003 | Grinberg et al. | |
| 2004/0002761 A1 | 1/2004 | Rogers et al. | |
| 2004/0002762 A1 | 1/2004 | Hawkins | |
| 2004/0006391 A1 | 1/2004 | Reiley | |
| 2004/0024462 A1 | 2/2004 | Ferree et al. | |
| 2004/0030390 A1 | 2/2004 | Ferree | |
| 2004/0030391 A1 | 2/2004 | Ferree | |
| 2004/0049190 A1 | 3/2004 | Biedermann et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049279 A1 | 3/2004 | Sevrain | |
| 2004/0049281 A1 | 3/2004 | Reiley | |
| 2004/0138749 A1 | 7/2004 | Zucherman et al. | |
| 2004/0181284 A1 | 9/2004 | Simonson | |
| 2004/0181285 A1 | 9/2004 | Simonson | |
| 2005/0033439 A1 * | 2/2005 | Gordon et al. | 623/17.16 |
| 2005/0143820 A1 | 6/2005 | Zucherman et al. | |
| 2005/0149196 A1 | 7/2005 | Zucherman et al. | |
| 2005/0154462 A1 | 7/2005 | Zucherman et al. | |
| 2005/0154464 A1 | 7/2005 | Eisermann et al. | |
| 2005/0154465 A1 | 7/2005 | Peterman et al. | |
| 2005/0154466 A1 | 7/2005 | Eisermann et al. | |
| 2005/0154467 A1 | 7/2005 | Peterman et al. | |
| 2005/0171608 A1 | 8/2005 | Peterman et al. | |
| 2005/0171609 A1 | 8/2005 | Humphreys et al. | |
| 2005/0171610 A1 | 8/2005 | Humphreys et al. | |
| 2005/0192671 A1 | 9/2005 | Bao et al. | |
| 2005/0234551 A1 | 10/2005 | Fallin et al. | |
| 2005/0234555 A1 | 10/2005 | Sutton et al. | |
| 2005/0240270 A1 | 10/2005 | Zubok et al. | |
| 2005/0256578 A1 | 11/2005 | Blatt et al. | |
| 2005/0261773 A1 | 11/2005 | Ferree | |
| 2005/0277930 A1 | 12/2005 | Parsons | |
| 2005/0277938 A1 | 12/2005 | Parsons | |
| 2005/0283237 A1 | 12/2005 | Zucherman et al. | |
| 2006/0009849 A1 | 1/2006 | Reiley | |
| 2006/0036325 A1 | 2/2006 | Paul et al. | |
| 2006/0069438 A1 | 3/2006 | Zucherman et al. | |
| 2006/0069440 A1 | 3/2006 | Zucherman et al. | |
| 2006/0085076 A1 | 4/2006 | Krishna et al. | |
| 2006/0089717 A1 | 4/2006 | Krishna et al. | |
| 2006/0178745 A1 | 8/2006 | Bartish, Jr. et al. | |

FOREIGN PATENT DOCUMENTS

| | | |
|---|---|---|
| DE | 20 2004 015198 | 11/2004 |
| EP | 0 677 277 A2 | 10/1995 |
| EP | 1 281 361 A1 | 2/2003 |
| FR | 2 676 911 A1 | 12/1992 |
| FR | 2 799 638 | 4/2001 |
| WO | WO 96/00049 | 1/1996 |
| WO | WO 99/53871 | 10/1999 |
| WO | WO 00/04851 | 2/2000 |
| WO | WO 01/39678 | 6/2001 |
| WO | WO 01/45576 | 6/2001 |
| WO | WO 02/47586 | 6/2002 |
| WO | WO 03/041618 A2 | 5/2003 |
| WO | WO 03/045262 A2 | 6/2003 |
| WO | WO 03/084449 | 10/2003 |
| WO | WO 03/101350 | 12/2003 |
| WO | WO 2004/034935 | 4/2004 |
| WO | WO 2004/041131 | 5/2004 |
| WO | WO 2004/098465 | 11/2004 |
| WO | WO 2005/112835 | 12/2005 |

OTHER PUBLICATIONS

Patent Cooperation Treaty—European Patent Office, "Notification of Transmittal of the International Search Report and the Written Opinion of the International Searching Authority, or the Declaration," International Application No. PCT/US2005/000705, Jun. 6, 2005, 7 pages.

Patent Cooperation Treaty—European Patent Office, "Invitation to Pay Additional Fees/Communication Relating to the Results of the Partial International Search," International Application No. PCT/US2005/000586, Jun. 8, 2005, 5 pages.

Patent Cooperation Treaty—European Patent Office, "Notification of Transmittal of the International Search Report and the Written Opinion of the International Searching Authority, or the Declaration," International Application No. PCT/US2005/000585, Jun. 8, 2005, 6 pages.

U.S. Appl. No. 11/342,961, filed Jan. 30, 2006, Yu, et al.
U.S. Appl. No. 11/343,159, filed Jan. 30, 2006, Braddock, Jr. et al.
U.S. Appl. No. 11/393,488, filed Mar. 30, 2006, Yu, et al.
U.S. Appl. No. 11/494,311, filed Jul. 27, 2006, Yu, et al.
Patent Cooperation Treaty—European Patent Office, "Notification of Transmittal of the International Search Report and the Written Opinion of the Internatinal Searching Authority, or the Declaration," International Application No. PCT/US2005/000704, Aug. 23, 2005, 7 pages.

Patent Cooperation Treaty—European Patent Office, "Notification of Transmittal of the International Search Report and the Written Opinion of the International Searching Authority, or the Declaration," International Application No. PCT/US2005/000656, Aug. 23, 2005, 8 pages.

* cited by examiner

DUAL ARTICULATING SPINAL DEVICE AND METHOD

CROSS-REFERENCE

This application claims priority from U.S. Provisional Patent Application Ser. No. 60/534,960 filed on Jan. 9, 2004, entitled "Posterior Lumbar Arthroplasty." The following applications also claim priority to the above referenced provisional application and are related to the present application. They are incorporated by reference herein.

- U.S. Utility patent application Ser. No. 11/031,602, filed on Jan. 7, 2005 and entitled "Spinal Arthroplasty Device and Method;"
- U.S. Utility patent application Ser. No. 11/031,780, filed on Jan. 7, 2005 and entitled "Split Spinal Device and Method;"
- U.S. Utility patent application Ser. No. 11/031,904, filed on Jan. 7, 2005 and entitled "Interconnected Spinal Device and Method;"
- U.S. Utility patent application Ser. No. 11/031,783, filed on Jan. 7, 2005 and entitled "Mobile Bearing Spinal Device and Method;"
- U.S. Utility patent application Ser. No. 11/031,700, filed on Jan. 7, 2005 and entitled "Support Structure Device and Method;"
- U.S. Utility patent application Ser. No. 11/031,781, filed on Jan. 7, 2005 and entitled "Centrally Articulating Spinal Device and Method;" and
- U.S. Utility patent application Ser. No. 11/031,903, filed on Jan. 7, 2005 and entitled "Posterior Spinal Device and Method."

TECHNICAL FIELD

Embodiments of the invention relate generally to devices and methods for accomplishing spinal surgery, and more particularly in some embodiments, to spinal arthroplasty devices capable of being placed posteriorly into the vertebral disc space. Various implementations of the invention are envisioned, including use in total spine arthroplasty replacing, via a posterior approach, both the disc and facet functions of a natural spinal joint.

BACKGROUND

As is known the art, in the human anatomy, the spine is a generally flexible column that can take tensile and compressive loads, allows bending motion and provides a place of attachment for ribs, muscles and ligaments. Generally, the spine is divided into three sections: the cervical, the thoracic and the lumbar spine. FIG. 1 illustrates schematically the lumbar spinal 1 and the sacrum regions 3 of a healthy, human spinal column. The sections of the spine are made up of individual bones called vertebrae and the vertebrae are separated by intervertebral discs which are situated therebetween.

FIG. 2 illustrates a portion of the right side of a lumbar spinal region with a healthy intervertebral disc 5 disposed between two adjacent vertebrae 7, 9. In any given joint, the top vertebra may be referred to as the superior vertebra and the bottom one as the inferior vertebra. Each vertebra comprises a generally cylindrical body 7a, 9a, which is the primary area of weight bearing, and three bony processes, e.g., 7b, 7c, 7d (two of which are visible in FIG. 2). As shown in FIG. 7A, in which all of the processes are visible, processes 7b, 7c, 7d extend outwardly from vertebrae body 7 at circumferentially spaced locations. The processes, among other functions, provide areas for muscle and ligament attachment. Neighboring vertebrae may move relative to each other via facet components 7e (FIG. 2), which extend from the cylindrical body of the vertebrae and are adapted to slide one over the other during bending to guide movement of the spine. There are two facet joints, each defined by upper and lower facet components, associated with adjacent vertebra. A healthy intervertebral disc is shown in FIG. 3. As shown in FIG. 3, an intervertebral disc has 4 regions: a nucleus pulposus 11, a transition zone 13, an inner annulus fibrosis region 15 and an outer annulus fibrosis 17. Generally, the inner annulus fibrosis region 15 and the outer annulus fibrosis region 17 are made up of layers of a fibrous gristly material firmly attached to the vertebral bodies above and below it. The nucleus pulposus 11 is typically more hydrated in nature.

These intervertebral discs function as shock absorbers and as joints. They are designed to absorb the compressive and tensile loads to which the spinal column may be subjected while at the same time allowing adjacent vertebral bodies to move relative to each other a limited amount, particularly during bending (flexure) of the spine. Thus, the intervertebral discs are under constant muscular and/or gravitational pressure and generally are the first parts of the lumbar spine to show signs of "wear and tear".

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

One surgical procedure for treating these conditions is spinal arthrodesis (i.e., spine fusion), which has been performed both anteriorally and/or posteriorally. The posterior procedures include in-situ fusion, posterior lateral instrumented fusion, transforaminal lumbar interbody fusion ("TLIF") and posterior lumbar interbody fusion ("PLIF"). Solidly fusing a spinal segment to eliminate any motion at that level may alleviate the immediate symptoms, but for some patients maintaining motion may be advantageous. It is also known to surgically replace a degenerative disc or facet joint with an artificial disc or an artificial facet joint, respectively. However, none of the known devices or methods provide the advantages of the embodiments of the present disclosure.

Accordingly, the foregoing shows there is a need for an improved spinal arthroplasty that avoids the drawbacks and disadvantages of the known implants and surgical techniques.

SUMMARY

In one embodiment, an artificial spinal joint creates at least a portion of a coupling between a superior vertebra and an inferior vertebra. The artificial spinal joint comprises an anterior joint replacement component extending into an intervertebral disc space between the superior and inferior vertebrae. The artificial spinal joint further comprises a bridge component coupled to the anterior joint replacement and extending posteriorly from the anterior joint replacement beyond the intervertebral disc space and a posterior joint replacement component coupled to the bridge, wherein the posterior joint replacement component includes a posterior protrusion engaged with a posterior socket.

In a second embodiment, a spinal arthroplasty device for interposition between a superior vertebra and an inferior vertebra comprises a rostral anterior component movably engaged with a caudal anterior component. The device further comprises a rostral posterior socket engaged with a caudal posterior posterior protrusion and configured to limit translation of the rostral anterior component relative to the caudal anterior component. In this embodiment, the rostral anterior component is connected to the rostral posterior component.

In a third embodiment, a method of implanting an artificial spinal joint comprises making a first incision in a patient's back, removing at least a portion of a spinal disc from an intervertebral space, inserting at least a portion of the artificial spinal joint through the incision, positioning an anterior joint portion of the artificial spinal joint in the intervertebral space, and positioning a posterior joint portion of the artificial spinal joint outside of the intervertebral space. The step of positioning a posterior joint portion includes engaging a posterior protrusion with a posterior socket.

In a fourth embodiment, a modular artificial spinal joint for interposition between a superior vertebra and an inferior vertebra comprises an anterior joint replacement component extending into an intervertebral disc space between the superior and inferior vertebrae. The modular artificial spinal joint further comprises a bridge component removably coupled to the anterior joint replacement and extending posteriorly from the anterior joint replacement beyond the intervertebral disc space and a posterior joint replacement component removably coupled to the bridge, wherein the posterior joint replacement component includes a posterior protrusion engaged with a posterior socket.

The embodiments disclosed may be useful for degenerative changes of the lumbar spine, post-traumatic, discogenic, facet pain or spondylolisthesis, and/or to maintain motion in multiple levels of the lumbar spine.

Additional and alternative features, advantages, uses and embodiments are set forth in or will be apparent from the following description, drawings, and claims.

DESCRIPTION

The drawings illustrate various embodiments of an artificial intervertebral joint for replacing an intervertebral disc or the combination of an intervertebral disc and at least one corresponding facet joint. Various embodiments of the artificial intervertebral joint according to the principles of the disclosure may be used for treating any of the problems that lend themselves to joint replacement including particularly, for example, degenerative changes of the lumbar spine, post-traumatic, discogenic, facet pain or spondylolisthesis and/or to maintain motion in multiple levels of the lumbar spine.

Figure 1:
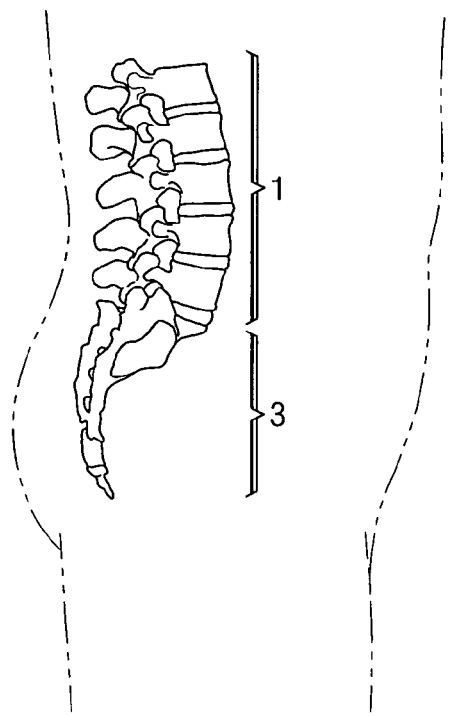
FIG. 1 is a side elevation schematic view of the lumbar spinal and the sacrum regions of a healthy, human spinal column.
Figure 2:
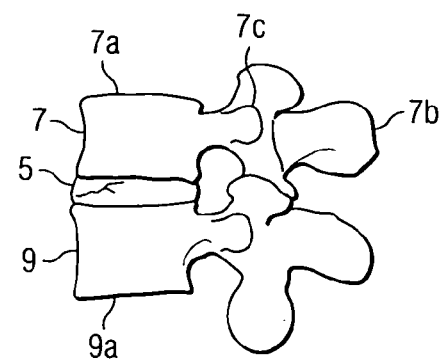
FIG. 2 is a detailed perspective view showing a portion of the right side of the lumbar vertebrae shown in FIG. 1 with a healthy disc disposed between two vertebrae.
Figure 3:
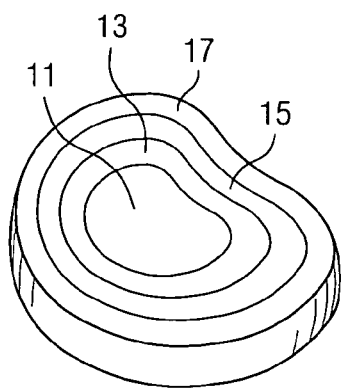
FIG. 3 is a top perspective view of the intervertebral disc shown in FIG. 2 illustrating the major portions of the disc.
Figure 4:
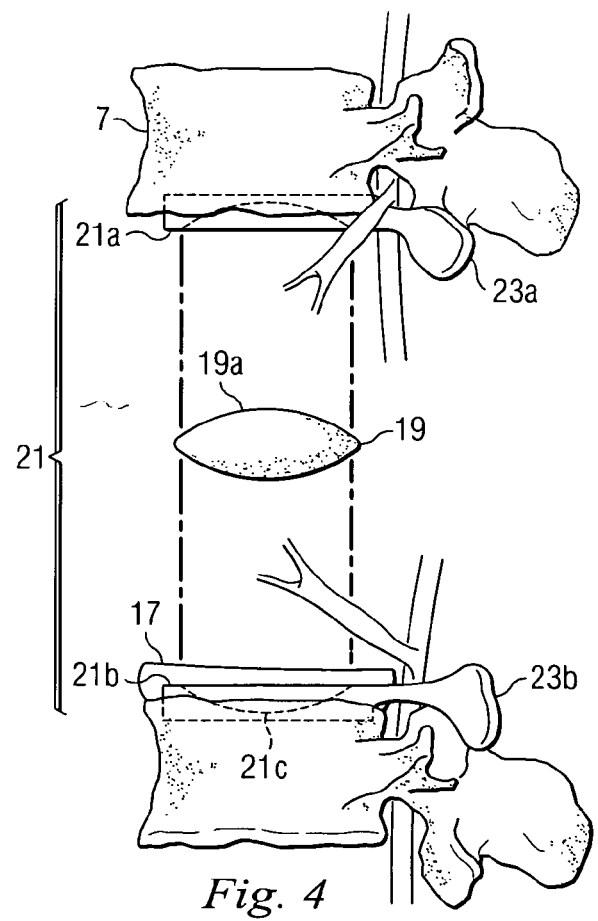
FIG. 4 is a side exploded elevation view of a portion of a lumbar spine showing a first embodiment of an artificial intervertebral joint constructed according to the principles of the disclosure.
Figure 5:
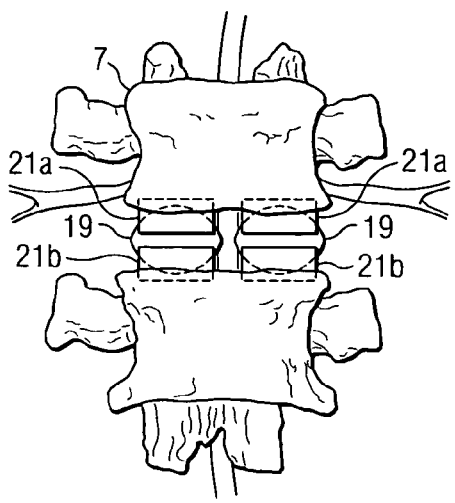
FIG. 5 is an anterior elevation view of a portion of a lumbar spine showing the superior, disc and inferior portions of the left and right halves of an assembled artificial intervertebral joint constructed according to the first embodiment of the disclosure.

FIGS. 4-7 illustrate a first exemplary embodiment of an artificial intervertebral joint. As illustrated in FIGS. 4 and 5, each joint is composed of two arthroplasty halves, each of which has a spacer or disc 19 and a retaining portion 21. The retaining portion 21 includes a first retaining portion 21a and a second retaining portion 21b. In the example illustrated in FIG. 4, the first retaining portion 21a is superior to (above) the second retaining portion 21b and the disc 19 is situated therebetween. Although the artificial intervertebral joint according to this exemplary embodiment has two halves for each of the first retaining portion and the second retaining portion, it should be understood that alternative embodiments may be implemented such that the artificial intervertebral joint has a single first retaining member, a single second retaining member and a single spacer. It should also be understood that alternative embodiments may also be carried out with arthroplasties having a first retaining portion, a second retaining portion, and/or a disc which each consist of unequal sized halves or more than two components.

Further, as illustrated in FIG. 4, the first retaining portion 21a and the second retaining portion 21b are situated between two adjacent vertebrae. More particularly, the first retaining portion may be situated along an inferior surface of the upper of the two adjacent vertebrae and the second retaining portion may be situated above a superior surface of the lower of the two adjacent vertebrae. However, it should be understood by one of ordinary skill in the art that the first retaining portion and second retaining portion are not limited to such an arrangement, and may be oriented in different positions and/or shaped differently than what is illustrated herein.

The surfaces of the retaining portions 21a, 21b of the arthroplasty that contact the remaining end plates of the vertebrae may be coated with a beaded material or plasma sprayed to promote bony ingrowth and a firm connection therebetween. In particular, the surface to promote bone ingrowth may be a cobalt chromium molybdenum alloy with a titanium/calcium/phosphate double coating, a mesh surface, or any other effective surface finish. Alternatively or in combination, an adhesive or cement such as polymethylmethacrylate (PMMA) may be used to fix all or a portion of the implants to one or both of the endplates.

As discussed in more detail below, a significant portion of the outer annulus region 17 (see, e.g., FIGS. 4, 7B), in some embodiments about 300 degrees, may be retained on the inferior portion of the end plate, which acts as a stop retaining the lower retaining portions in place until bone ingrowth occurs to firmly attach the retaining portions to their respective vertebrae (FIG. 4 only shows a portion of the outer annulus 17 that is retained). In contrast, in conventional anterior arthroplasty about 270 degrees of the outer annulus region 17 typically is removed. In addition, pedicle screws may also be used for immediate fixation as described in more detail in connection with other embodiments discussed below.

In the various embodiments of this disclosure, the first retaining portion 21a and the second retaining portion 21b are structured so as to retain the disc 19 therebetween. For example, in the case of a disc 19 with two convex surfaces 19a, each of the first retaining portion 21a and the second retaining portion 21b may have a concave surface 21c which defines a space within which the disc 19 may be retained. For example, in the exemplary embodiment shown in FIG. 4, the upper convex surface 19a of the disc 19 fits within the concavity defined by the concave surface 21c of the first retaining portion 21a and the lower convex surface 19b of the disc 19 fits within the concavity defined by the concave surface 21c of the second retaining portion 21b.

Figure 6:
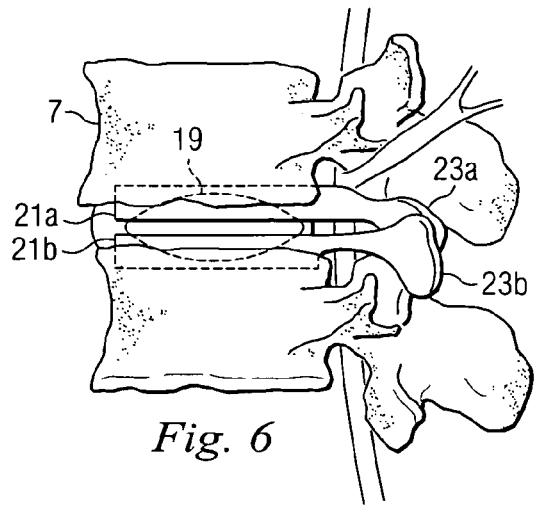
FIG. 6 is a side elevation view of the right half of the artificial intervertebral joint shown in FIG. 5.

FIG. 5 illustrates an anterior view of an exemplary assembled artificial intervertebral joint with both arthroplasty halves in place, and FIG. 6 shows a side view of the assembled artificial intervertebral joint shown in FIG. 5. As illustrated in FIGS. 5 and 6, the disc 19 is retained between the first retaining portion 21a and the second retaining portion 21b. It should be understood that although the disc 19 may be held between the first retaining portion 21a and the second retaining portion 21b, the disc 19 is free to slidably move within the space defined by the corresponding surfaces 21a of the first retaining portion 21a and the second retaining portion 21b. In this manner, limited movement between the adjacent vertebrae is provided.

In the exemplary embodiment illustrated in FIGS. 4, 5 and 6, the disc 19 is a separate component which is inserted between the first retaining portion 21a and the second retaining portion 21b. However, as discussed below, it should be understood that the spacer or disc 19 may be integrally formed with or integrated into in one or both of the first retaining portion 21a and the second retaining portion 21b.

Figure 7A:
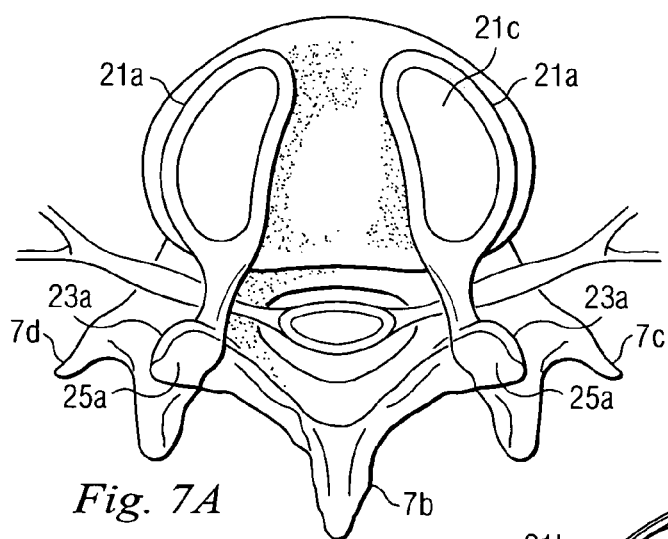
FIG. 7A is a transverse, bottom-up-view of a portion of a lumbar spine showing the superior portion of the artificial intervertebral joint illustrated in FIG. 4.
Figure 7B:
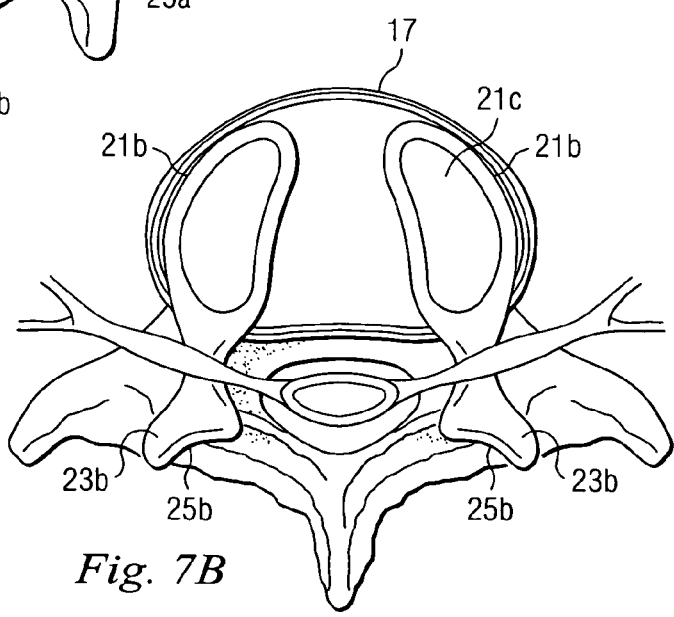
FIG. 7B is a transverse, top-down-view of a portion of a lumbar spine showing the inferior portion of the artificial intervertebral joint illustrated in FIG. 4.
Figure 8:
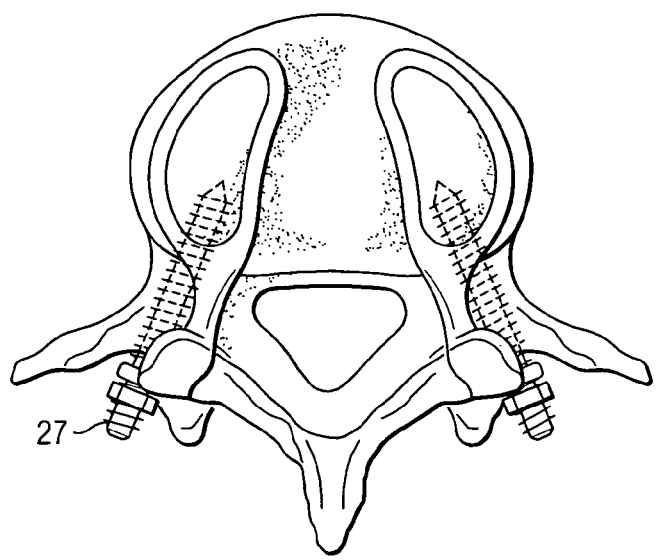
FIG. 8 is a transverse, bottom-up-view of a portion of a lumbar spine showing a second embodiment of a superior portion of an artificial intervertebral joint in which pedicle screws are used to assist in implantation.
Figure 9:
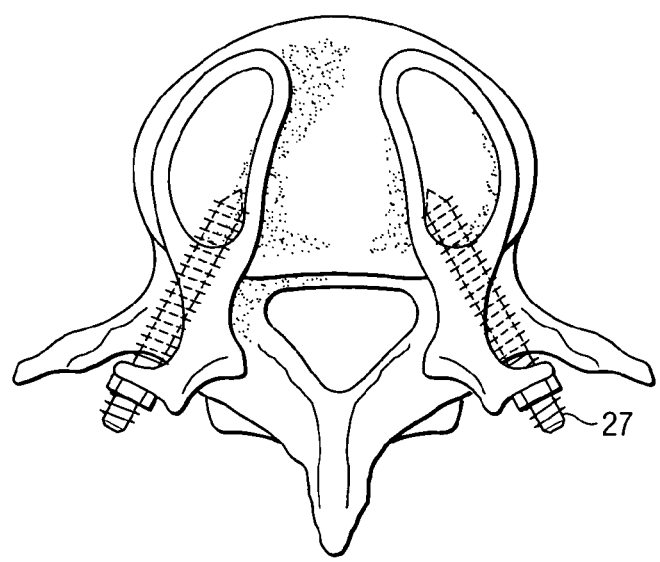
FIG. 9 is a transverse, top-down-view of a portion of a lumbar spine showing a second embodiment of an inferior portion of an artificial intervertebral joint in which pedicle screws are used to assist in implantation.
Figure 10:
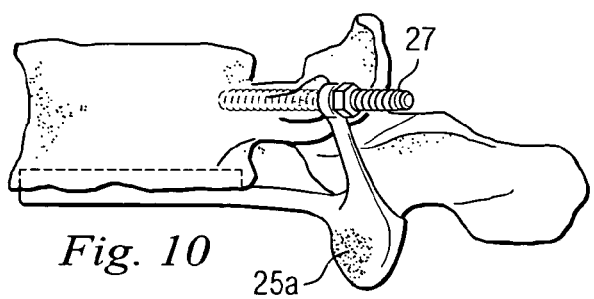
FIG. 10 is a lateral view of a portion of a lumbar spine showing the superior portion of the artificial intervertebral joint shown in FIG. 8 with one of the pedicle screws being visible.
Figure 11:
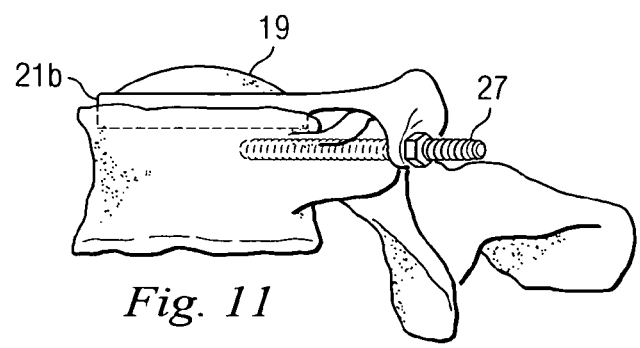
FIG. 11 is a lateral view of a portion of a lumbar spine showing the inferior and integrated disc portions of an artificial integral intervertebral joint shown in FIG. 9 with one of the pedicle screws being visible.
Figure 12:
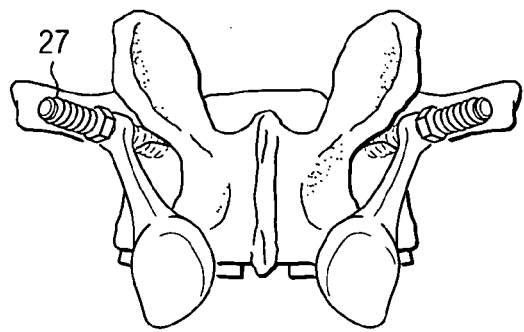
FIG. 12 is a posterior view of a portion of a lumbar spine showing the superior portion of the artificial intervertebral joint shown in FIG. 8 with two pedicle screws being visible.
Figure 13:
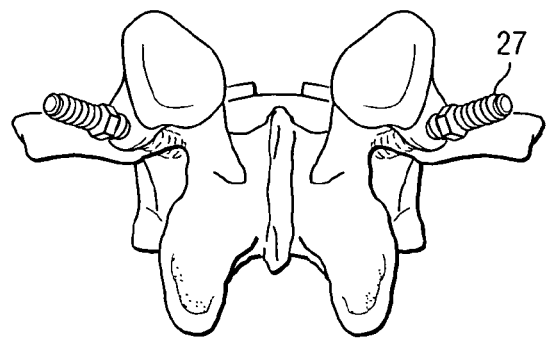
FIG. 13 is a posterior view of a portion of a lumbar spine showing the inferior portion of the artificial intervertebral joint shown in FIG. 9 with two pedicle screws being visible.

In the exemplary embodiment of the disclosure, as illustrated best in FIGS. 4, 6, 7A and 7B, each of the retaining portions of the artificial intervertebral joint includes a first artificial facet component 23a and a second artificial facet component 23b. As shown in FIGS. 7A and 7B, the first artificial facet component 23a has a face 25a and the corresponding second artificial facet component 23b has a face 25b configured such that the face 25a matingly fits with the face 25b to stabilize adjacent vertebrae while preserving and guiding the mobility of each vertebrae with respect to the other vertebrae. Each set of the upper and lower retaining portions 21a, 21b may have a pair of facet components 23a, 23b, which together define a facet joint. For a total joint replacement with facets according to this embodiment, the left and right arthroplasties would define two adjacent facet joints when viewed from the posterior.

Regardless of whether artificial facet joints are provided, the respective upper and lower retaining portions associated with the left and right halves of the arthroplasty may be completely independent from the other. That is, as shown in FIG. 7A, for example, the first retaining portions 21a associated with each half are not in direct contact with each other. The same is true with respect to the second retaining portions 21b shown in FIG. 7B. However, it should be understood by one of ordinary skill in the art that, even in the embodiment of the disclosure which includes artificial facet joints, at least a portion of the first retaining portions 21a of each half and/or at least a portion of the second retaining portions 21b of each half may directly contact and/or be connected to each other as described in more detail in connection with the discussion of FIGS. 17-18.

Further, in the various embodiments of the disclosure, the disc 19, the first retaining portion 21a and the second retaining portion 21b may be made of any appropriate material which will facilitate a connection that transmits compressive and tensile forces while providing for the aforementioned slidable motion in a generally transverse direction between each of the adjacent surfaces. For example, in the first embodiment, the first retaining portion 21a and the second retaining portion 21b may be typically made from any metal or metal alloy suitable for surgical implants such as stainless steel, titanium, and cobalt chromium, or composite materials such as carbon fiber, or a plastic material such as polyetheretherketone (PEEK) or any other suitable materials. The disc may be made from plastic such as high molecular weight polyethylene or PEEK, or from ceramics, metal, and natural or synthetic fibers such as, but not limited to, carbon fiber, rubber, or other suitable materials. Generally, to help maintain the sliding characteristic of the surfaces, the surfaces may be polished and/or coated to provide smooth surfaces. For example, if the surfaces are made of metal, the metal surfaces may be polished metal.

FIGS. 8-14 illustrate a second embodiment of an artificial intervertebral joint. Only features that differ from the first embodiment are discussed in detail herein. In the second exemplary embodiment, securing components, such as, for example, pedicle screws 27 are provided to provide a more secure and immediate connection between each of the first retaining portion 21a and/or the second retaining portion 21b to the corresponding vertebra. In addition, this embodiment illustrates a disc 19 which is integrated with one of the retaining portions, here lower retaining portion 21b. Disc 19 may be integrally formed from the same material as its retaining portion, but also may be separately formed from similar or dissimilar materials and permanently connected thereto to form an integral unit. In this embodiment, the disc 19 and the retaining portions may be all formed from metal.

Figure 15:
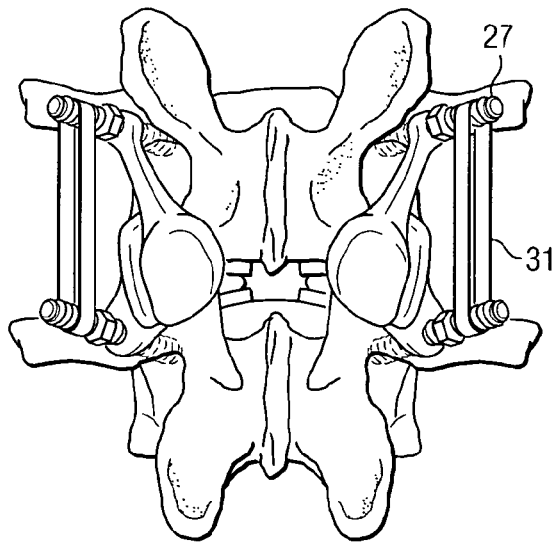
FIG. 15 is a posterior view of a portion of a lumbar spine showing a third embodiment of the inferior, disc and superior portions of an artificial intervertebral joint in which tension bands are used.
Figure 16:
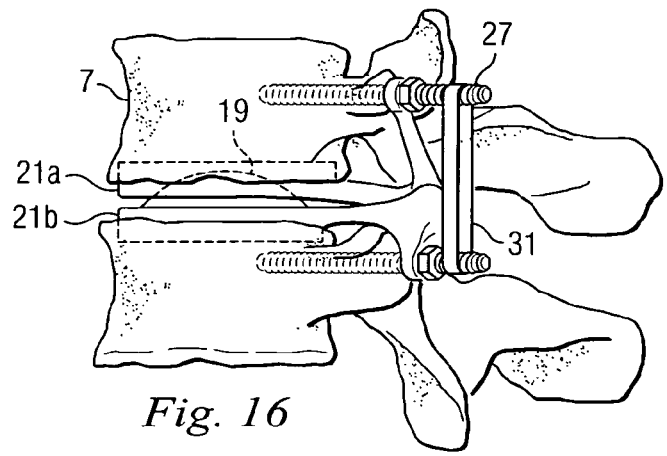
FIG. 16 is a side elevation view of a portion of a lumbar spine showing the third embodiment in which tension bands are used in an assembled position.

FIGS. 15 and 16 illustrate a third embodiment of an artificial intervertebral joint. In the third exemplary embodiment, additional securing components, such as, for example, tension bands 31 are provided to supplement or replace the function of posterior ligaments that limit the mobility between adjacent vertebrae by securing the first retaining portion 21a to the second retaining portion 21b. As shown in FIGS. 15-16, posterior tension bands 31 may be provided by wrapping them around the corresponding pedicle screws 27 or other convenient attachment points.

Figure 17:
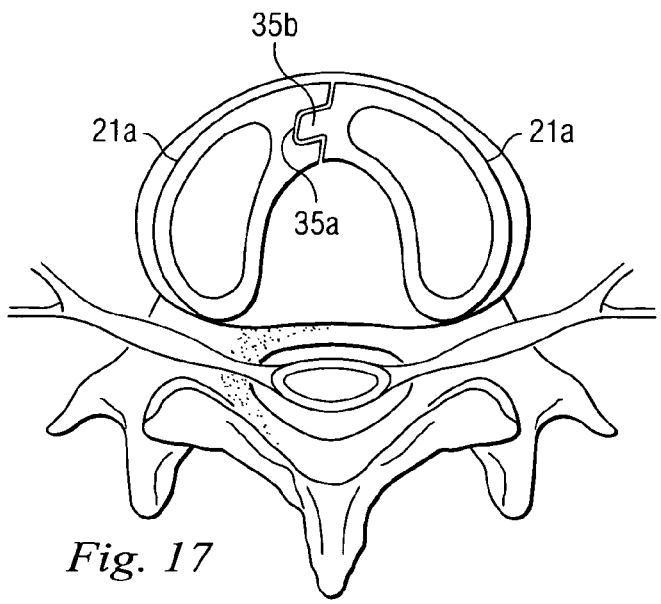
FIG. 17 is a transverse, bottom-up-view of a portion of a lumbar spine showing the superior portion of a fourth embodiment of an artificial intervertebral joint constructed according to the principles of the disclosure in which the facet joints are not replaced.
Figure 18:
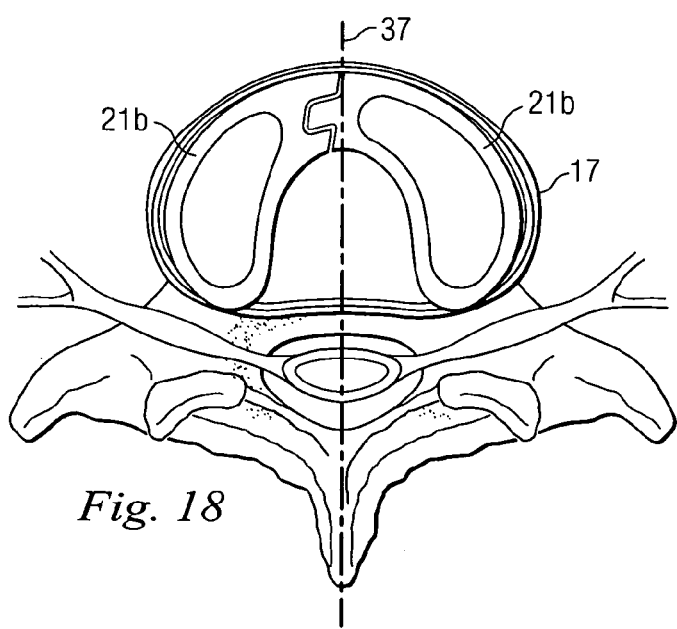
FIG. 18 is a transverse, top-down-view of a portion of a lumbar spine showing the inferior portion of the fourth embodiment of an artificial intervertebral joint.

FIGS. 17 and 18 illustrate a fourth embodiment of an artificial intervertebral joint. In the exemplary embodiment illustrated in FIGS. 17 and 18, the artificial intervertebral joint may have all of the features discussed above except for artificial facet components. In this embodiment, the natural facet joints remain. The ligamentous tension band may also be left intact in some embodiments. In addition, this embodiment includes a specific example of an anterior midline connection between respective upper and lower retaining portions, which assists in maintaining the placement of the first retaining portion 21a and the second retaining portion 21b.

FIGS. 17 and 18 illustrate that it is possible to provide a first retaining portion 21a with a lock and key type pattern which is complemented by the corresponding mating portion provided on the second retaining portion 21b. More particularly, one half of the first retaining portion 21a has an outer boundary with a U-shaped portion 35a while the other half of the corresponding first retaining portion 21a has an outer boundary with a protruding portion 35b, which fits into the U-shaped portion 35a. As a result, each half of the first retaining portion 21a, 21b may be maintained in a predetermined position. However, the upper or lower retaining portions may fit together and/or be connected in the interbody space, e.g., near their midline anterior portions, in any manner that facilitates implantation and/or assists in providing and/or retaining the joint in a generally stable, symmetrical configuration. It may be even more important to provide such connection between the lower retaining portions due to the inward forces provided by annulus 17 remaining on the inferior end plate as shown in FIG. 18. A midline connection between the respective lower retaining portions will resist the force of the outer annulus tending to cause migration of the retaining portions toward the midline 37.

As shown in the various exemplary embodiments, other than the portions of the first and/or second retaining portions which may fit together like a lock and key to maintain the placement of the portions relative to each other, each half of the artificial intervertebral joint may be generally symmetrical about the midline 37 of the vertebrae.

Again, these exemplary embodiments are merely illustrative and are not meant to be an exhaustive list of all possible designs, implementations, modifications, and uses of the invention. Moreover, features described in connection with one embodiment of the disclosure may be used in conjunction with other embodiments, even if not explicitly stated above.

While it should be readily apparent to a skilled artisan from the discussion above, a brief description of a suitable surgical procedure that may be used to implant the artificial joint is provided below. Generally, as discussed above, the artificial intervertebral joint may be implanted into a body using a posterior transforaminal approach similar to the known TLIF or PLIF procedures. According to this approach, an incision, such as a midline incision, may be made in the patient's back and some or all of the affected disc and surrounding tissue may be removed via the foramina. Depending on whether any of the facet joints are being replaced, the natural facet joints may be trimmed to make room for the artificial facet joints. Then, the halves of the artificial intervertebral joint may be inserted piecewise through the left and right transforaminal openings, respectively. That is, the pieces of the artificial intervertebral joint including the upper and lower retaining portions, with or without facet components, and the artificial disc, if provided separately, fit through the foramina and are placed in the appropriate intervertebral space. The pieces of the artificial joint may be completely separated or two or more of them may be tied or packaged together prior to insertion through the foramina by cloth or other materials known in the art. In cases where at least a portion of the outer annulus of the natural disc can be retained, the lower retaining portions of each side of the artificial intervertebral joint are inserted such that they abut a corresponding portion of the annulus. If a midline anterior connection is provided, the left and right halves of the retaining members are fitted together and held in place by the outer annulus. As such, the remaining portion of the annulus may be in substantially the same place as it was prior to the procedure.

Further, in the cases where the annulus of the natural disc must be removed completely or this is insufficient annulus remaining, it is possible, for example, to use the embodiment of the disclosure where the pedicle screws are implemented so as to be assured that the pieces of the artificial intervertebral joint remain in place. It should be understood by one of ordinary skill in the art that the artificial joint could be implanted via an anterior approach or a combined anterior and posterior approach, although the advantages of a posterior procedure would be limited. For example, some of the pieces of the artificial intervertebral joint may be inserted from an anterior approach and others posteriorly. The anteriorly and posteriorly placed portions could be fitted together similar to the embodiment shown in FIGS. 17 and 18.

Figure 19:
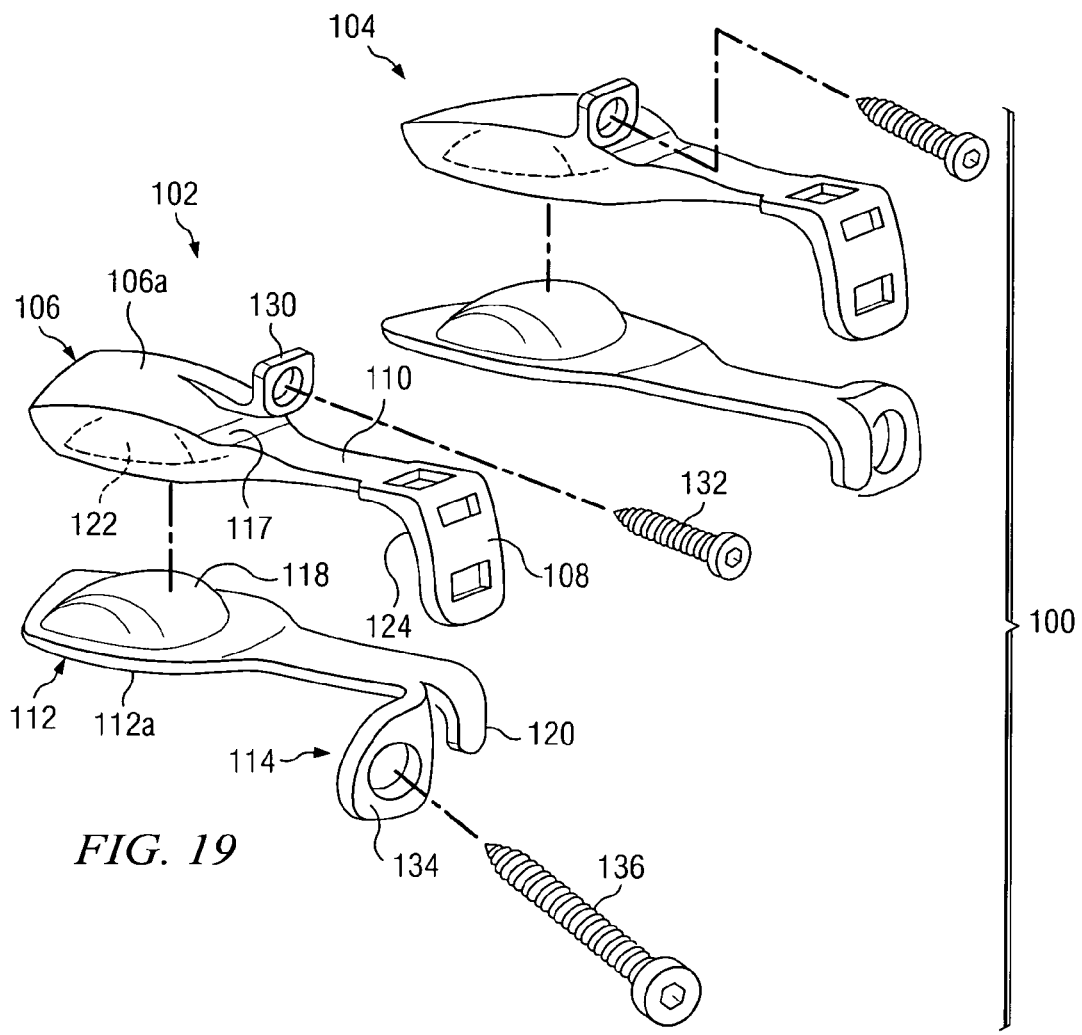
FIG. 19 is an exploded perspective view of another embodiment of the present disclosure.
Figure 20:
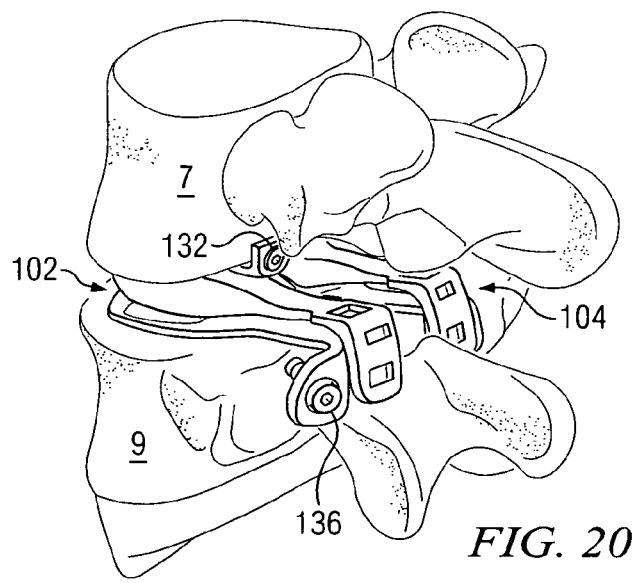
FIG. 20 is an assembled side elevation of the embodiment of FIG. 19.

Referring now to FIGS. 19 and 20, in this embodiment, an artificial intervertebral joint 100 may include two arthroplasty halves 102, 104 which may be inserted between the vertebrae 7, 9. The arthroplasty half 102 may include a rostral anterior joint component 106, a rostral posterior joint component 108, and a rostral bridge 110 extending between the anterior component 106 and the posterior component 108.

The arthroplasty half 102 may further include a caudal anterior joint component 112, a caudal posterior joint component 114, and a caudal bridge 116 extending between the anterior component 112 and the posterior component 114. The rostral anterior joint component 106 may include a bone contacting surface 106a and the caudal anterior joint component 112 may include a bone contacting surface 112a. The arthroplasty half 104 may be substantially similar in structure and function to the arthroplasty half 102 and therefore will not be described in further detail.

The terms "rostral" and "caudal" are used in some embodiments to describe the position of components of the embodiments. While rostral is typically used in the art to describe positions toward the head and caudal is used to describe positions toward the tail or foot, as used herein, rostral and caudal are used simply as modifiers for the relative locations of components of the illustrated embodiments. For example, rostral components may be on one side of an illustrated joint, and caudal may be on another side of the joint. Components labeled as rostral or caudal to describe an illustrated embodiment are not intended to limit the orientation of a device or application of a method relative to a patient's anatomy, or to limit the scope of claims to any device or method.

In this embodiment, the rostral bridge 110 may include a jog 117 to create an exit portal and an artificial foramen for the exiting nerve root. Either of the bridges 110, 116, but particularly the caudal bridge 116, may be a "super" or artificial pedicle which may supplement or replace a natural pedicle. Also in this embodiment, the caudal anterior joint component 112 may include a curved protrusion 118, and the caudal posterior joint component 114 may include a posterior protrusion 120. The rostral anterior joint component 106 may include an anterior socket 122 configured to receive the curved protrusion 118. A radius of curvature for the curved protrusion 118 may closely match the radius of curvature for the anterior socket 122 to create a highly constrained ball and socket type engagement. In an alternative embodiment, by increasing the radius of curvature for the socket relative to the radius of the curved protrusion, the curved protrusion may be permitted to translate within the socket.

The rostral posterior joint component 108 may include a posterior socket 124 configured to engage the posterior protrusion 120. A radius of curvature for the posterior protrusion 120 may be smaller than a radius of curvature for the posterior socket 124, thereby permitting motion and limiting binding between the posterior joint components 108, 114. The radii of curvature for the posterior socket 124 and the posterior protrusion 120 may emanate from a common center of rotation for the arthroplasty half 102. In this embodiment, the radius of curvature for the posterior socket 124 is relatively large, and the resulting joint is loosely constrained. In an alternative embodiment, a tight radius of curvature for the posterior protrusion of the caudal posterior component matched with a rostral posterior component having a tight radius of curvature may create a tightly constrained posterior joint.

The size and shape of the anterior components 106, 112 and the bridge components 110, 116 may be limited by the constraints of a posterior surgical approach. For example, the anterior components 106, 112 may be configured to cover a maximum vertebral endplate area to dissipate loads and reduce subsidence while still fitting through the posterior surgical exposure, Kambin's triangle, and other neural elements. To achieve maximum surface coverage, the material of the anterior components 106, 112 may extend anteriorly from the curved protrusion 118 and the anterior socket 122, respectively. The width of the bridge components 110, 116 are also minimized to pass through Kambin's triangle and to co-exist with the neural elements.

The arthroplasty half 102 further includes features for affixing to the vertebrae 7, 9. It is understood, however, that in an alternative embodiment, the fixation features may be eliminated. Arthroplasty half 102 may include a connection component 130 extending rostrally from the rostral anterior joint component 106. The connection component 130 in this embodiment is an aperture adapted to receive a bone fastener such as screw 132. The orientation of the connection component 130 permits the screw 132 to affix to the cylindrical vertebral body 7a. In an alternative embodiment, the rostral connection component may permit connection with the pedicle of vertebra 7 as shown, for example, in FIG. 14. A few alternative embodiments for the rostral connection component will be described below.

Arthroplasty half 102 may further include a connection component 134 attached to or integrally formed with the caudal posterior joint component 114. The connection component 134 in this embodiment is an aperture adapted to receive a bone fastener such as screw 136. The orientation of the connection component 134 permits the screw 136 to become inserted extrapedicularly such that the screw travels a path angled or skewed away from a central axis defined through a pedicle. Extrapedicular fixation may be any fixation into the pedicle that does not follow a path down a central axis defined generally posterior-anterior through the pedicle. In this embodiment, the screw passes through a lateral wall of the pedicle and may achieve strong cortical fixation. In all embodiments, the screws may be recessed so as not to interfere with articulations, soft tissues, and neural structures.

Figure 14:
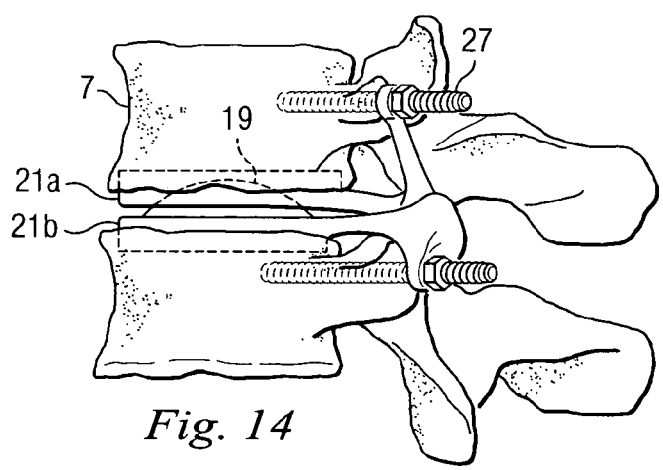
FIG. 14 is a side elevation view of a portion of a lumbar spine showing the second embodiment with pedicle screws in an assembled position.

In an alternative embodiment, for example as shown in FIG. 14, a connection component extending from the posterior component 114 may be oriented to permit the screw to become inserted intrapedicularly such that the screw travels a path generally along the central axis through the pedicle. In still another alternative embodiment, the posterior connection component may connect to the generally cylindrical body portion 9a. It is understood that in other alternative embodiments, the connection components may extend at a variety of angles, in a variety of directions from the various components of the arthroplasty half. For example, a connection component may extend from the rostral bridge rather than the rostral anterior joint component.

As shown in FIGS. 19 and 20, the rostral components 106, 108, 110 of the arthroplasty half 102 are integrally formed. It is understood that in a modular alternative embodiment, these components may be removably coupled to one another. For example, the rostral anterior joint component may be installed separate from the bridge. After the anterior component is in place, the bridge may be attached to the anterior component by any fastening mechanism known in the art, for example a threaded connection, a bolted connection, or a latched connection. A modular rostral posterior component may then be attached by a similar fastening mechanism to the bridge to complete the rostral portion of the arthroplasty half.

A modular embodiment of the artificial intervertebral joint may be particularly suited to revision applications in which, for example, the anterior components located between the bodies 7a, 9a may be installed in a first surgical procedure and the bridge and/or posterior components may be added in later surgeries to further correct or supplement the function of the artificial intervertebral joint. Thus, modular bridge and/or posterior components may added to a variety of artificial intervertebral joints from a variety of different manufacturers. For example, components similar to those described in this disclosure may be used to revise artificial intervertebral joints including those described in U.S. Pat. No. 6,740,118; and U.S. patent application Publication Nos. 2004/0158328; 2004/0073312; and 2003/0204261, all assigned to SDGI Holdings, Inc. of Wilmington, Del. and incorporated by reference herein; the ProDisc® System described in part by U.S. Pat. No. 5,314,477 and U.S. patent application Publication No. 2004/0117022 (all incorporated by reference herein) and marketed by Spine Solutions, Inc. a subsidiary of Synthes, Inc. of Oberdorf, Switzerland; or the Charité™ Artificial Disc described in part by U.S. Pat. Nos. 4,759,766; 4,997,432; 5,401,269; 5,556,431; and 6,416,551 (all incorporated by reference herein) and marketed by DePuy Spine™, a Johnson & Johnson company. Similarly, modular bridge and/or posterior components may be adapted to be added to any other motion anterior component or to any fusion anterior component.

The arthroplasty halves 102, 104 may be formed of any suitable biocompatible material including metals such as cobalt-chromium alloys, titanium alloys, nickel titanium alloys, and/or stainless steel alloys. Ceramic materials such as aluminum oxide or alumnia, zirconium oxide or zirconia, compact of particulate diamond, and/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. The various components comprising the arthroplasty halves 102, 104 may be formed of different materials thus permitting metal on metal, metal on ceramic, metal on polymer, ceramic on ceramic, ceramic on polymer, or polymer on polymer constructions.

Bone contacting surfaces of the arthroplasty halves 102, 104 may include features or coatings which enhance the fixation of the implanted prosthesis. For example, the surfaces may be roughened such as by chemical etching, bead-blasting, sanding, grinding, serrating, and/or diamond-cutting. All or a portion of the bone contacting surfaces of the arthroplasty halves 102, 104 may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes, ridges, and/or other surface textures.

The artificial intervertebral joint 100 may be installed between the vertebrae 7, 9 as will be described below. Although installation will be described with respect to arthroplasty half 102, it is understood that the arthroplasty half 104 may be installed in a similar manner. Generally, as discussed above, the artificial intervertebral joint 100 may be implanted into a body using a posterior transforaminal approach similar to the known TLIF or PLIF procedures. PLIF approaches are generally more medial and rely on more retraction of the traversing root and dura to access the vertebral interspace. The space between these structures is known as Kambin's triangle. TLIF approaches are typically more oblique, requiring less retraction of the exiting root, and less epidural bleeding with less retraction of the traversing structures. It is also possible to access the interspace using a far lateral approach, above the position of the exiting nerve root and outside of Kambin's triangle. In some instances it is possible to access the interspace via the far lateral without resecting the facets.

Furthermore, a direct lateral approach through the psoas is known. This approach avoids the posterior neural elements completely. Embodiments of the current invention are anticipate that could utilize any of these common approaches.

According to at least one of these approaches, an incision, such as a midline incision, may be made in the patient's back and some or all of the affected disc and surrounding tissue may be removed via the foramina. The superior endplate surface of the vertebra 9 may be milled, rasped, or otherwise resected to match the profile of the caudal anterior bone contacting surface 112a, to normalize stress distributions on the superior endplate surface of the vertebra 9, and/or to provide initial fixation prior to bone ingrowth. The preparation of the endplate of vertebra 9 may result in a flattened surface or in surface contours such as pockets, grooves, or other contours that may match corresponding features on the bone contacting surface 112a. The inferior endplate of the vertebra 7 may be similarly prepared to receive the rostral anterior joint component 106 to the extent allowed by the exiting nerve root and the dorsal root ganglia. Depending on whether any of the facet joints are being replaced, the natural facet joints of vertebrae 7, 9 may be trimmed to make room for the posterior components 108, 114.

The halves 102, 104 of the artificial intervertebral joint 100 may then be inserted piecewise through the left and right transforaminal openings, respectively. That is, the pieces of the artificial intervertebral joint 100 including the rostral and caudal anterior joint components 106, 112 respectively fit through the foramina and are placed in the appropriate intervertebral disc space between the generally cylindrical bodies 7a, 9a. The pieces of the artificial joint 100 may be completely separated or two or more of them may be tied or packaged together prior to insertion through the foramina by cloth or other materials known in the art. In cases where at least a portion of the outer annulus of the natural disc can be retained, the caudal anterior joint components of each side of the artificial intervertebral joint are inserted such that they abut a corresponding portion of the annulus. The bridges 110, 116 may extend posteriorly from the anterior joint components 106, 112 and posteriorly from the intervertebral disc space. The posterior components 108, 114 are positioned posteriorly of the intervertebral disc space to replace or supplement the function of the natural facet joints. The screw 132 may be inserted through the connection component 130 and into the generally cylindrical body 7a, and the screw 136 may be inserted through the connection component 134 and into adjacent bone such as the pedicle. It is understood that the screws may be implanted either after the entire arthroplasty half 102 has been implanted or after each of the rostral and caudal component has been implanted.

As installed, the anterior ball and socket type joint created by the rostral anterior joint component 106 and the caudal anterior joint component 112 may be relatively stable and self-centering. Both the anterior joint and the posterior joint, created by the rostral posterior joint component 108 and the caudal posterior joint component 114, allow the arthroplasty half 102 to resist shear forces, particularly anterior-posterior forces. Movement of the rostral anterior joint component 106 relative to the caudal anterior joint component 112 may be limited by the displacement of the posterior protrusion 120 within the posterior socket 124. For example, lateral translation of the rostral anterior joint component 106 relative to the caudal anterior joint component 112 may be limited by the posterior joint. Rotational motion about a longitudinal axis defined by the cylindrical bodies 7a, 9a may be limited both by the constraint in the posterior joint and by the combined constraint provided by the two arthroplasty halves 102, 104. Further, the posterior joint may restrict any true lateral bending degree of freedom.

Pure freedom of motion may be limited to flexion-extension motion about an axis defined through the anterior joints of the arthroplasty halves 102, 104. However, under certain conditions, the joint 100 may overcome these design restrictions to permit limited lateral, rotational, and coupled movements. For example, the anterior joint components 106, 112 may become disconnected or disarticulated from each other and experience limited "lift-off," thereby permitting additional degrees of freedom and coupled motions beyond strict flexion-extension motion. The self-centering nature of the anterior joint may encourage reconnection and alignment after lift-off occurs. The limited disconnection of the anterior joint components 106, 112 may be accommodated by the degree of constraint in the posterior joint. For example, relatively loose constraint in the posterior joint permits greater amounts of lift-off. Some degree of constraint in the posterior joint may be useful, however, to encourage reconnection and alignment of the anterior joint.

In general, a simple, anteriorly located ball and socket joint which is tightly constrained with each component having the same or similar radii of curvature may allow flexion-extension, lateral bending, and torsion motions while resisting shear forces and limiting translation. By adding an additional highly constrained ball and socket joint to the posterior components, an additional degree of freedom may be limited, such as torsion. Additional joints may further limit degrees of freedom of motion. If the anterior or posterior joints are permitted to disconnect or disarticulate additional degrees of freedom may be permitted as described above. Changing the shape of or clearance between the ball and socket components will also permit additional degrees of motion.

The robust and forgiving structure of the anterior and posterior joints also permits misalignment and slight inaccuracy in the placement of the arthroplasty halves 102, 104. For example, the self-aligning ball and socket structure of the anterior joint components 106, 112 tolerates a certain amount of misalignment between the components. Thus, the insertion trajectories for the components 106, 112 may be slightly misaligned. The interaction of the posterior protrusion 120 and the posterior socket 124 may also accommodate parallel misalignment and/or anterior-posterior misalignment between the arthroplasty halves 102, 104.

In an alternative embodiment, a single unilateral arthroplasty half may be installed. This type of intentional lateralization of the anterior articulation may create a wedge effect that may be desirable to treat scoliosis or other pathologic conditions that require balance correction. In circumstances in which both arthroplasty halves are installed, scoliosis and similar pathologic conditions may be remedied by using anterior components of different heights and shapes. In this way, the articulating joint replacement assembly may act as a wedge, creating a different intervertebral height than the support joint replacement assembly.

Figure 21:
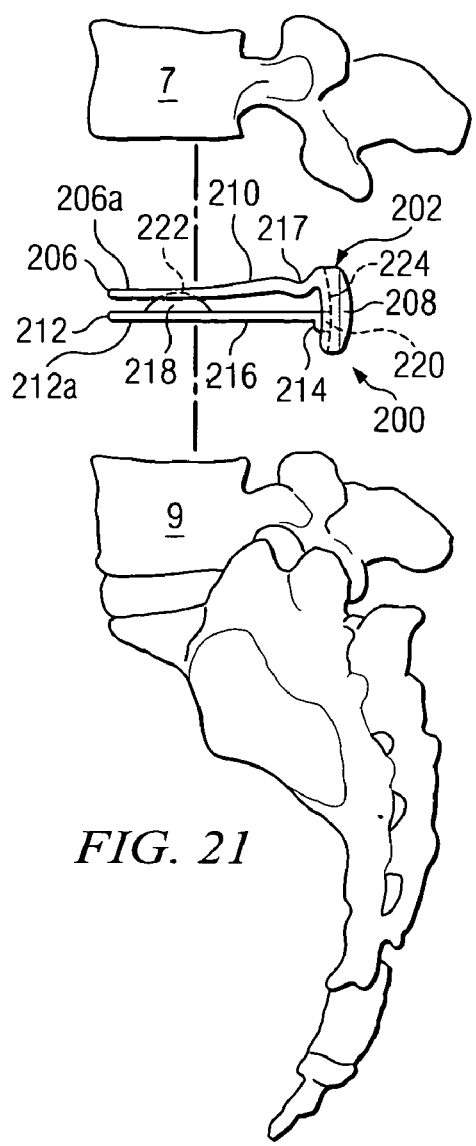
FIG. 21 is an exploded side elevation view of another embodiment of the present disclosure.
Figure 22:
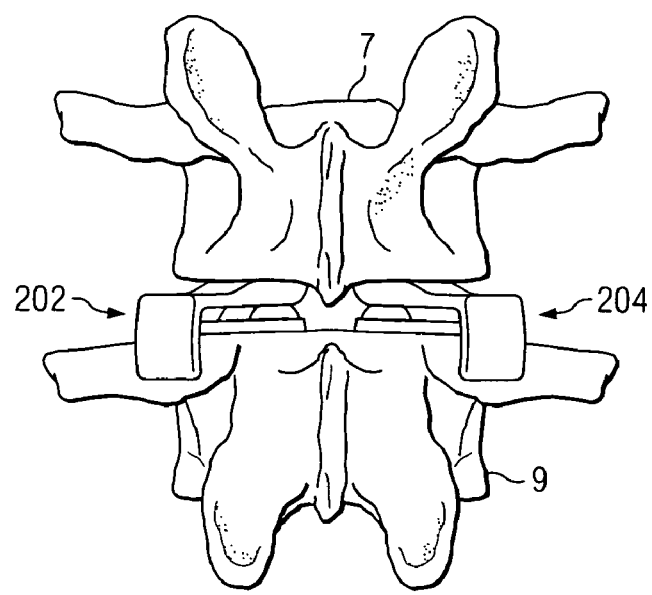
FIG. 22 is a posterior elevation view of the embodiment of FIG. 21.

Referring now to FIGS. 21 and 22, in this embodiment, an artificial intervertebral joint 200 may include two arthroplasty halves 202, 204 which may be inserted between the vertebrae 7, 9. The arthroplasty half 202 may include a rostral anterior joint component 206, a rostral posterior joint component 208, and a rostral bridge 210 extending between the anterior component 206 and the posterior component 208. The arthroplasty half 202 may further include a caudal anterior joint component 212, a caudal posterior joint component 214, and a caudal bridge 216 extending between the anterior component 212 and the posterior component 214. The rostral anterior joint component 206 may include a bone contacting surface 206a and the caudal anterior joint component 212 may include a bone contacting surface 212a. The arthroplasty half 204 may be substantially similar in structure and function to the arthroplasty half 202 and therefore will not be described in further detail.

In this embodiment, the rostral bridge 210 may include a jog 217 to create an exit portal and an artificial foramen for the exiting nerve root. Also in this embodiment, the caudal anterior joint component 212 may include a curved protrusion 218, and the caudal posterior joint component 214 may include a posterior protrusion 220. The rostral anterior joint component 206 may include an anterior socket 222 configured to receive the curved protrusion 218. A radius of curvature for the curved protrusion 218 may closely match the radius of curvature for the anterior socket 222 to create a highly constrained ball and socket type engagement. In an alternative embodiment, by increasing the radius of curvature for the socket relative to the radius of the curved protrusion, the curved protrusion may be permitted to translate within the socket.

The rostral posterior joint component 208 may include a posterior socket 224 configured to engage the posterior protrusion 220. A radius of curvature for the posterior protrusion 220 may be smaller than a radius of curvature for the posterior socket 224, thereby permitting motion and limiting binding between the posterior joint components 208, 214. The radii of curvature for the posterior socket 224 and the posterior protrusion 220 may emanate from a common center of rotation for the arthroplasty half 202. In this embodiment, the radius of curvature for the posterior socket 224 is relatively large, and the resulting joint is loosely constrained. In an alternative embodiment, a tight radius of curvature for the posterior protrusion of the caudal posterior component matched with a rostral posterior component having a tight radius of curvature may create a tightly constrained posterior joint.

The size and shape of the anterior components 206, 212 and the bridge components 210, 216 may be limited by the constraints of a posterior surgical approach. For example, the anterior components 206, 212 may be configured to cover a maximum vertebral endplate area to dissipate loads and reduce subsidence while still fitting through the posterior surgical exposure, Kambin's triangle, and other neural elements. To achieve maximum surface coverage, the material of the anterior components 206, 212 may extend anteriorly from the curved protrusion 218 and the anterior socket 222. The width of the bridge components 210, 216 are also minimized to pass through Kambin's triangle and to co-exist with the neural elements.

In this embodiment, connection components are omitted. However, it is understood that in an alternative embodiment, connection components substantially similar to those described above may be used.

As shown in FIGS. 21 and 22, the rostral components 206, 208, 210 of the arthroplasty half 202 are integrally formed. It is understood that in a modular alternative embodiment, these components may be removably coupled to one another. For example, the rostral anterior joint component may be installed separate from the bridge. After the anterior component is in place, the bridge may be attached to the anterior component by any fastening mechanism known in the art, for example a threaded connection, a bolted connection, or a latched connection. A modular rostral posterior component may then be attached by a similar fastening mechanism to the bridge to complete the rostral portion of the arthroplasty half.

The arthroplasty halves 202, 204 may be formed of any suitable biocompatible material including the metals, ceramics, or polymers described above. Further, any of the bone contacting surfaces of the arthroplasty halves 202, 204 may be treated with the coatings or features described above.

The artificial intervertebral joint 200 may be installed between the vertebrae 7, 9 as will be described below. Although installation will be described with respect to arthroplasty half 202, it is understood that the arthroplasty half 204 may be installed in a similar manner. Generally, as discussed above, the artificial intervertebral joint 200 may be implanted into a body using a posterior transforaminal approach similar to the known TLIF or PLIF procedures. PLIF approaches are generally more medial and rely on more retraction of the traversing root and dura to access the vertebral interspace. The space between these structures is known as Kambin's triangle. TLIF approaches are typically more oblique, requiring less retraction of the exiting root, and less epidural bleeding with less retraction of the traversing structures. It is also possible to access the interspace using a far lateral approach, above the position of the exiting nerve root and outside of Kambin's triangle. In some instances it is possible to access the interspace via the far lateral without resecting the facets. Furthermore, a direct lateral approach through the psoas is known. This approach avoids the posterior neural elements completely. Embodiments of the current invention are anticipate that could utilize any of these common approaches.

According to at least one of these approaches, an incision, such as a midline incision, may be made in the patient's back and some or all of the affected disc and surrounding tissue may be removed via the foramina. The superior endplate surface of the vertebra 9 may be milled, rasped, or otherwise resected to match the profile of the caudal anterior bone contacting surface 212a, to normalize stress distributions on the superior endplate surface of the vertebra 9, and/or to provide initial fixation prior to bone ingrowth. The preparation of the endplate of vertebra 9 may result in a flattened surface or in surface contours such as pockets, grooves, or other contours that may match corresponding features on the bone contacting surface 212a. The inferior endplate of the vertebra 7 may be similarly prepared to receive the rostral anterior joint component 206 to the extent allowed by the exiting nerve root and the dorsal root ganglia. Depending on whether any of the facet joints are being replaced, the natural facet joints of vertebrae 7, 9 may be trimmed to make room for the posterior components 208, 214.

The halves 202, 204 of the artificial intervertebral joint 200 may then be inserted piecewise through the left and right transforaminal openings, respectively. That is, the pieces of the artificial intervertebral joint 200 including the rostral and caudal anterior joint components 206, 212 respectively fit through the foramina and are placed in the appropriate intervertebral disc space between the generally cylindrical bodies 7a, 9a. The pieces of the artificial joint 200 may be completely separated or two or more of them may be tied or packaged together prior to insertion through the foramina by cloth or other materials known in the art. In cases where at least a portion of the outer annulus of the natural disc can be retained, the caudal anterior joint components of each side of the artificial intervertebral joint are inserted such that they abut a corresponding portion of the annulus. The bridges 210, 216 may extend posteriorly from the anterior joint components 206, 212 and posteriorly from the intervertebral disc space. The posterior components 208, 214 are positioned posteriorly of the intervertebral disc space to replace or supplement the function of the natural facet joints.

As installed, the anterior ball and socket type joint created by the rostral anterior joint component 206 and the caudal anterior joint component 212 may be relatively stable and self-centering. Both the anterior joint and the posterior joint, created by the rostral posterior joint component 208 and the caudal posterior joint component 214, allow the arthroplasty half 202 to resist shear forces, particularly anterior-posterior forces. Movement of the rostral anterior joint component 206 relative to the caudal anterior joint component 212 may be limited by the displacement of the posterior protrusion 220 within the posterior socket 224. For example, lateral translation of the rostral anterior joint component 206 relative to the caudal anterior joint component 212 may be limited by the posterior joint. Rotational motion about a longitudinal axis defined by the cylindrical bodies 7a, 9a may be limited both by the constraint in the posterior joint and by the combined constraint provided by the two arthroplasty halves 202, 204. Further, the posterior joint may restrict any true lateral bending degree of freedom.

Pure freedom of motion may be limited to flexion-extension motion about an axis defined through the anterior joints of the arthroplasty halves 202, 204. However, under certain conditions, the joint 100 may overcome these design restrictions to permit limited lateral, rotational, and coupled movements. For example, the anterior joint components 206, 212 may become disconnected from each other and experience limited "lift-off," thereby permitting additional degrees of freedom and coupled motions beyond strict flexion-extension motion. The self-centering nature of the anterior joint may encourage reconnection and alignment after lift-off occurs. The limited disconnection of the anterior joint components 206, 212 may be accommodated by the degree of constraint in the posterior joint. For example, relatively loose constraint in the posterior joint permits greater amounts of lift-off. Some degree of constraint in the posterior joint may be useful, however, to encourage reconnection and alignment of the anterior joint.

The robust and forgiving structure of the anterior and posterior joints also permits misalignment and slight inaccuracy in the placement of the arthroplasty halves 202, 204. For example, the self-aligning ball and socket structure of the anterior joint components 206, 212 tolerates a certain amount of misalignment between the components. Thus, the insertion trajectories for the components 206, 212 may be slightly misaligned. The interaction of the posterior protrusion 220 and the posterior socket 224 may also accommodate parallel misalignment and/or anterior-posterior misalignment between the arthroplasty halves 202, 204.

Figure 23:
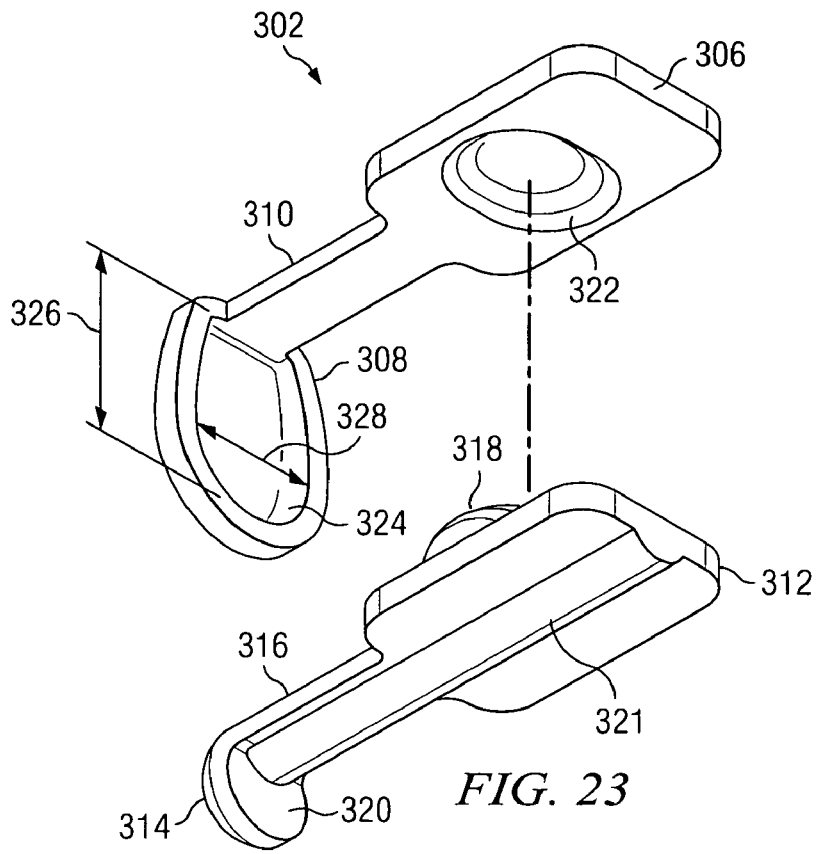
FIG. 23 is an exploded perspective view of another embodiment of the present disclosure.
Figure 24:
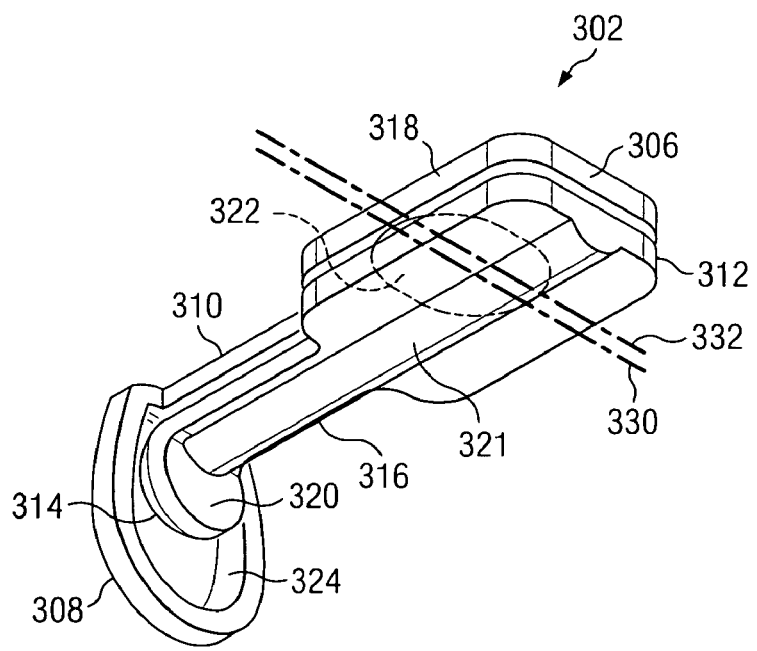
FIG. 24 is an assembled perspective view of the embodiment of FIG. 23.

Referring now to FIGS. 23 and 24, in another embodiment, an artificial intervertebral joint may include an arthroplasty half 302 which may be inserted between the vertebrae 7, 9 on one lateral side. A second arthroplasty half (not shown) may be inserted on the opposite lateral side and may have a similar configuration and function. The arthroplasty half 302 may include a rostral anterior joint component 306, a rostral posterior joint component 308, and a rostral bridge 310 extending between the anterior component 306 and the posterior component 308. The arthroplasty half 302 may further include a caudal anterior joint component 312, a caudal posterior joint component 314, and a caudal bridge 316 extending between the anterior component 312 and the posterior component 314.

In this embodiment, the caudal anterior joint component 312 may include a curved protrusion 318, and the caudal posterior joint component 314 may include a posterior protrusion 320. The rostral anterior joint component 306 may include an anterior socket 322 configured to receive the curved protrusion 318. The rostral posterior joint component 308 may include a posterior socket 324 shaped like a trough and configured to engage the posterior protrusion 320 such that the surface 320 is permitted to ride in the trough.

In this embodiment, a keel 321 may extend from the caudal anterior joint component 312 and along the caudal bridge 316. The keel 321 may allow the arthroplasty half 302 to engage the superior endplate of the vertebral body 9a and a superior face of a pedicle of vertebra 9. It is understood that the superior endplate of the body 9a and the pedicle of vertebra 9 may be milled, chiseled, or otherwise prepared to create a channel for receiving the keel 321. The keels may help to connect to the bone and limit movement of the arthroplasty half 302 to the desired degrees to freedom. The keels may have an angled or semi-cylindrical cross section. It is understood that more than one keel may be used on any given component.

The arthroplasty half 302 may be constructed of any of the materials described above for joint 100. Likewise, the bone contacting surfaces of the arthroplasty half 302 may be coated as described above for joint 100. Installation may also proceed in a manner substantially similar to that described for joint 100.

Without copying the exact structure of the natural facets, this embodiment may mimic many of the functions of the natural facet joints. In this embodiment, the arthroplasty half 302 may be largely controlled from the posterior, where mechanical advantage may be greatest. A rostral-caudal length 326 of the posterior socket 324 may limit the flexion extension range of motion while the lateral width 328 of the posterior socket may limit the rotational range of motion. For example, as shown in FIG. 23, where the length 326 is greater than the length of the posterior protrusion 320, a range of flexion-extension motion is permitted as the posterior protrusion 320 travels within the posterior socket 324. With little or no clearance between the posterior protrusion 320 and the width 328 of the posterior socket 324, rotational motion may be largely eliminated. Both the anterior joint and the posterior joint allow the arthroplasty half 302 to resist shear forces, particularly anterior-posterior forces.

In this embodiment, the anterior joint formed by the anterior socket 322 and the curved protrusion 318 may have a flexion-extension axis of rotation 330 positioned posteriorly relative to a midline 332 of the caudal anterior joint component 312. When installed between the vertebrae 7, 9, the axis 330 may also be positioned posteriorly relative to the longitudinal axis defined by the generally cylindrical bodies 7a, 9a, thus placing the center of motion in a more natural position.

Figure 25:
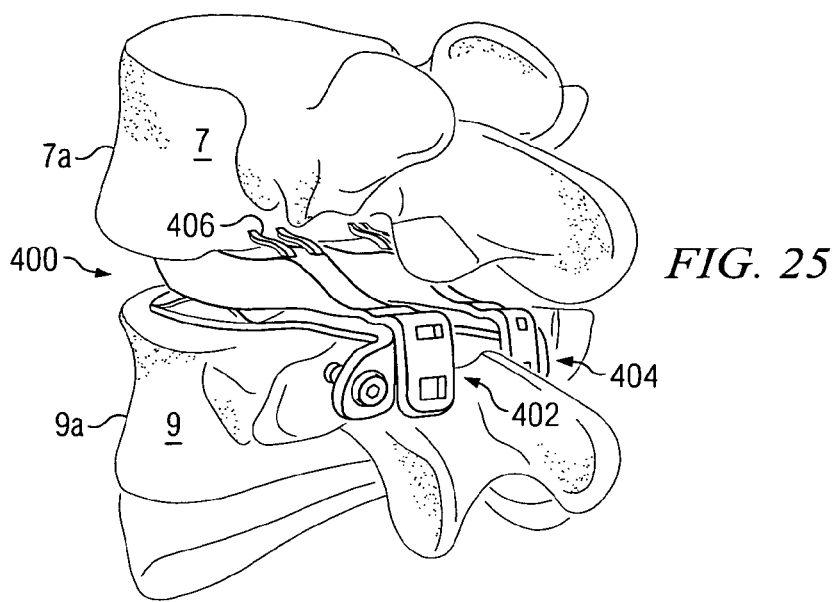
FIG. 25 is an assembled side elevation of another embodiment of the present disclosure.

Referring now to FIG. 25, in this embodiment, an artificial intervertebral joint 400 may include two arthroplasty halves 402, 404 which may be inserted between the vertebrae 7, 9. The joint 400 may be substantially similar to joint 100 except for the following differences. In this embodiment, the arthroplasty half 402 may include a rostral connection component 406 which may include a set of spikes or pins. As the arthroplasty half 402 is inserted between the vertebrae 7, 9, the spikes advance to engage the cylindrical body portion 7a.

Figure 26:
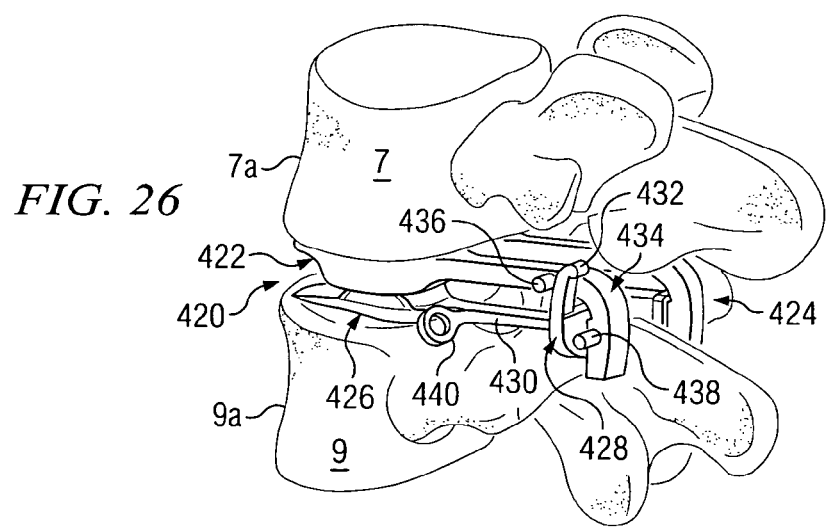
FIG. 26 is an assembled side elevation of another embodiment of the present disclosure.

Referring now to FIG. 26, in this embodiment, an artificial intervertebral joint 420 may include two arthroplasty halves 422, 424 which may be inserted between the vertebrae 7, 9. The joint 420 may be substantially similar to joint 100 except for the following differences. In this embodiment, the arthroplasty half 422 may include a caudal anterior joint component 426, a caudal posterior joint component 428, and a caudal bridge 430 extending between the components 426, 428. The caudal posterior joint component 428 may include a motion stop 432. The arthroplasty half 422 may also include a rostral posterior joint component 434 comprising motion stops 436, 438.

The posterior joint formed by components 428, 434 may be assembled such that motion stop 432 is positioned between motion stops 436, 438. Under anterior-posterior shear loads, displacement may be limited or prevented by the interaction of motion stop 436 against motion stop 432. Flexion-extension motion may be limited by the distance between the stops 436, 438, which act as motion limits for the motion stop 432.

The arthroplasty half 422 may further comprise a caudal connection component 440 extending from the caudal bridge 430. In this embodiment, the connection component 440 is angled such that a bone screw placed through the connection component engages the generally cylindrical body portion 9a.

Figure 27:
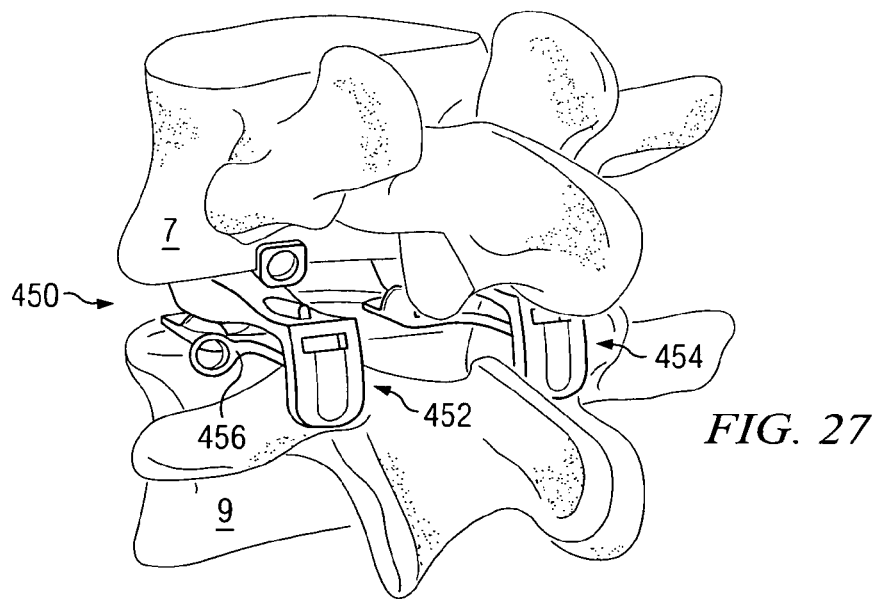
FIG. 27 is an assembled side elevation of another embodiment of the present disclosure.

Referring now to FIG. 27, in this embodiment an artificial intervertebral joint 450 may include two arthroplasty halves 452, 454 which may be inserted between the vertebrae 7, 9. The joint 450 may be substantially similar to joint 100 except for the following differences. In this embodiment, the arthroplasty half 452 may include a caudal connection component 456 which may include an aperture angled such that a bone screw inserted through the aperture engages the generally cylindrical body portion 9a.

Figure 28:
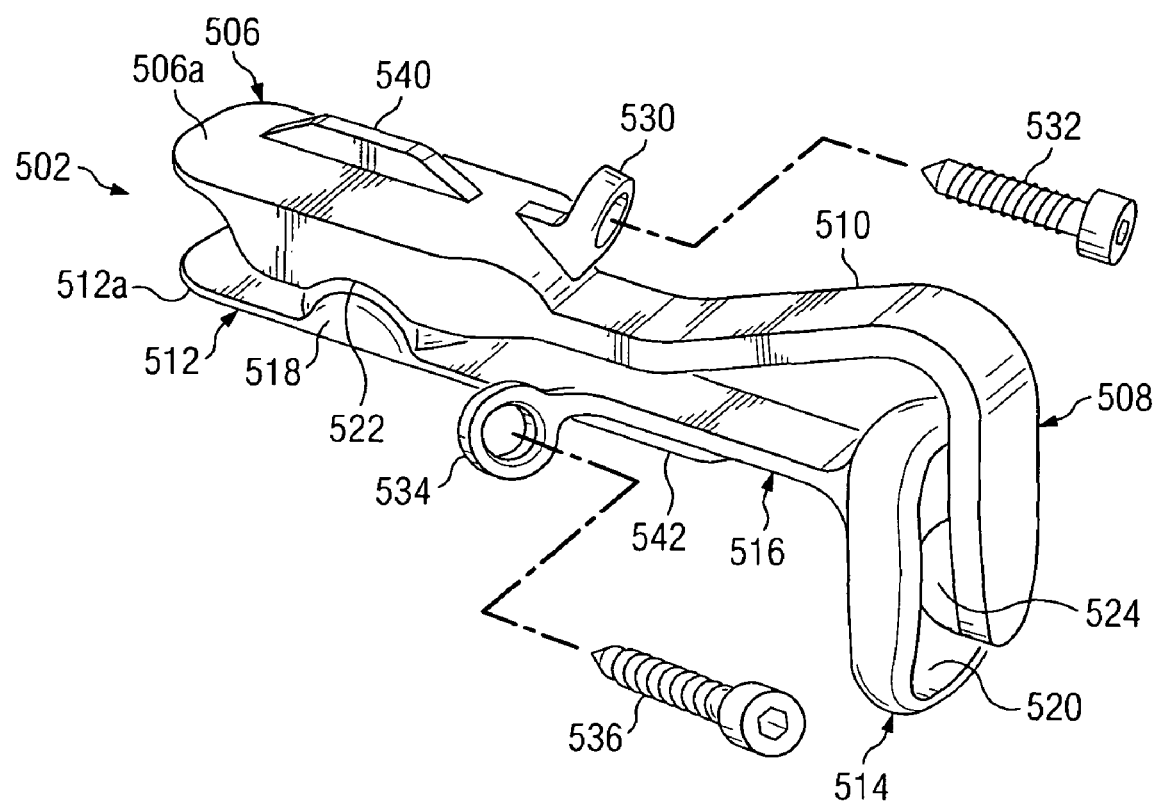
FIG. 28 is an assembled perspective view of another embodiment of the present invention.

Referring now to FIG. 28, in this embodiment, one arthroplasty half 502 of an artificial intervertebral joint may be inserted between the vertebrae 7, 9. It is understood that a second arthroplasty half (not shown) may be inserted on an opposite lateral side, similar to the embodiments described above. The arthroplasty half 502 may include a rostral anterior joint component 506, a rostral posterior joint component 508, and a rostral bridge 510 extending between the anterior component 506 and the posterior component 508. The arthroplasty half 502 may further include a caudal anterior joint component 512, a caudal posterior joint component 514, and a caudal bridge 516 extending between the anterior component 512 and the posterior component 514. The rostral anterior joint component 506 may include a bone contacting surface 506a and the caudal anterior joint component 512 may include a bone contacting surface 512a.

Also in this embodiment, the caudal anterior joint component 512 may include a curved protrusion 518, and the caudal posterior joint component 514 may include a posterior socket 520. The rostral anterior joint component 506 may include an anterior socket 522 configured to receive the curved protrusion 518.

The rostral posterior joint component 508 may include a posterior protrusion 524 configured to engage the posterior socket 520. In this embodiment, the posterior protrusion may be a partial sphere that may rotate or translate within the socket 520, forming a loosely constrained ball and socket style joint.

The arthroplasty half 502 may further include features for affixing to the vertebrae 7, 9. It is understood, however, that in an alternative embodiment, the fixation features may be eliminated. Arthroplasty half 502 may include a connection component 530 extending rostrally from the rostral anterior joint component 506. The connection component 530 in this embodiment is a tab with an aperture adapted to receive a bone fastener such as screw 532. The orientation of the connection component 530 permits the screw 132 to affix to the cylindrical vertebral body 7a. In an alternative embodiment, the rostral connection component may permit connection with the pedicle of vertebra 7 as shown, for example, in FIG. 14. Arthroplasty half 502 may further include a connection component 534 attached to or integrally formed with the caudal anterior joint component 512. The connection component 534 in this embodiment is a tab with an aperture adapted to receive a bone fastener such as screw 536. The orientation of the connection component 534 permits the screw 536 to affix to the cylindrical vertebral body 9a. The connection components 530, 534 may also function as support tabs, providing additional surface area to dissipate forces and reduce subsidence.

The arthroplasty half 502 may further include a rostral keel 540 extending from the rostral anterior joint component 506 and a caudal keel 542 extending from the caudal anterior joint component 512 and down the caudal bridge 516. The keel 540 may allow the arthroplasty half 502 to engage the inferior endplate of the vertebral body 7a, and the keel 542 may allow the arthroplasty half 502 to engage the superior endplate of the vertebral body 9a and a superior face of a pedicle of vertebra 9. It is understood that the inferior endplate of the body 7a may be milled or otherwise prepared to receive the keel 540. Likewise, the superior endplate of the body 9a and the pedicle of vertebra 9 may be milled, chiseled, or otherwise prepared to create a channel for receiving the keel 542. The keels may help to connect to the bone and limit movement of the arthroplasty half 502 to the desired degrees to freedom. The keels may have an angled or semi-cylindrical cross section. It is understood that more than one keel may be used on any given component.

The arthroplasty half 502 may be installed similarly to the arthroplasty half 102 and may have similar motion in the anterior joint. In this embodiment, the ball shaped posterior protrusion 524 may be positioned in the socket 520 which is elongated to permit flexion-extension motion while limiting torsion. Locating the protrusion 524 on the rostral component 508, may simplify installation as the surgeon's view of the socket 520 and his/her ability to assemble the posterior joint may be improved.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed is:

1. An artificial spinal joint for creating at least a portion of a coupling between a superior vertebra and an inferior vertebra comprising:
an anterior joint replacement component sized to extend into an intervertebral disc space between the superior and inferior vertebrae, wherein the anterior joint replacement component includes a left anterior member separated and spaced apart from a right anterior member;
a bridge component coupled at a first end to the anterior joint replacement and sized to extend posteriorly outside the intervertebral disc space, wherein the bridge component includes a left bridge member separated and spaced apart from a right bridge member; and
a posterior joint replacement component coupled to a second end of the bridge component, wherein the posterior joint replacement component includes a posterior protrusion engaged with a posterior socket, wherein the posterior joint replacement component includes a left posterior member separated and spaced apart from a right posterior member;
wherein the left posterior member includes a first posterior protrusion engaged with a first posterior socket and the right posterior member includes a second posterior protrusion engaged with a second posterior socket.

2. The artificial spinal joint of claim 1 wherein the anterior joint replacement component includes a rostral anterior component engaged with a caudal anterior component.

3. The artificial spinal joint of claim 2 wherein the bridge component comprises a rostral bridge extending from the rostral anterior component.

4. The artificial spinal joint of claim 2 wherein the bridge component comprises a caudal bridge extending from the caudal anterior component.

5. The artificial spinal joint of claim 1 wherein the posterior joint replacement component comprises:
a rostral posterior component, wherein the rostral posterior component includes the posterior socket and
a caudal posterior component, wherein the caudal posterior component includes the posterior protrusion.

6. The artificial spinal joint of claim 1 further comprising a bone fastener for attaching the artificial spinal joint to either the superior vertebra or the inferior vertebra.

7. The artificial spinal joint of claim 6 wherein the posterior joint replacement component comprises a connection component adapted to receive the bone fastener.

8. The artificial spinal joint of claim 7 wherein the bone fastener is a bone screw and the connection component is further adapted to direct the received bone screw extrapedicularly into a pedicle wall of the inferior vertebra.

9. The artificial spinal joint of claim 7 wherein the bone fastener is a bone screw and the connection component is further adapted to direct the received bone screw into a generally cylindrical body portion of the inferior vertebra.

10. The artificial spinal joint of claim 7 wherein the bone fastener is a bone screw and the connection component is further adapted to direct the received bone screw intrapedicularly along a central axis of a pedicle of the inferior vertebra.

11. The artificial spinal joint of claim 6 wherein the anterior joint replacement component comprises a connection component adapted to receive the bone fastener.

12. The artificial spinal joint of claim 11 wherein the bone fastener is a bone screw and the connection component is further adapted to direct the received bone screw into a generally cylindrical body portion of the superior vertebra.

13. The artificial spinal joint of claim 11 wherein the bone fastener is a bone screw and the connection component is further adapted to direct the received bone screw intrapedicularly along a central axis of a pedicle of the superior vertebra.

14. The artificial spinal joint of claim 6 wherein the bone fastener comprises a spike extending from the anterior joint replacement component, wherein the spike is adapted to engage a generally cylindrical body portion of the superior vertebra.

15. The artificial spinal joint of claim 6 wherein the bridge component comprises a connection component adapted to receive the bone fastener.

16. The artificial spinal joint of claim 1 wherein the anterior joint replacement component includes a curved protrusion engaged with an anterior socket.

17. The artificial spinal joint of claim 16 wherein the superior and inferior vertebrae comprise superior and inferior cylindrical bodies, respectively and wherein an axis of motion defined by the curved protrusion in engagement with the anterior socket is positioned posteriorly of a longitudinal axis defined by the superior and inferior cylindrical bodies.

18. The artificial spinal joint of claim 16 wherein the anterior joint replacement component includes a bone contacting surface extending anteriorly of the curved protrusion.

19. The artificial spinal joint of claim 1 wherein the anterior joint replacement component is sized for insertion through Kambin's triangle.

20. The artificial spinal joint of claim 1 wherein the posterior socket comprises an elongated trough.

21. The artificial spinal joint of claim 1 wherein the bridge component comprises a jog adapted to permit passage of a neural element.

22. The artificial spinal joint of claim 1 wherein a radius of curvature for the posterior protrusion is smaller than a radius of curvature for the posterior socket.

23. The artificial spinal joint of claim 1 wherein a radius of curvature for the posterior protrusion matches a radius of curvature for the posterior socket.

24. The artificial spinal joint of claim 1 wherein a radius of curvature for the curved protrusion matches a radius of curvature for the anterior socket.

25. The artificial spinal joint of claim 1 wherein a radius of curvature for the curved protrusion is smaller than a radius of curvature for the anterior socket.

26. The artificial spinal joint of claim 1 wherein the bridge component is at least a portion of an artificial pedicle.

27. The artificial spinal joint of claim 1 wherein the anterior joint component comprises a keel.

28. The artificial spinal joint of claim 1 wherein the bridge component comprises a keel adapted for engaging a pedicle.

29. The artificial spinal joint of claim 1 wherein the posterior joint replacement component comprises a rostral posterior component and a caudal posterior component and wherein the posterior protrusion is located on the rostral posterior component and the posterior socket is located on the caudal posterior component.

* * * * *